United States Patent
Bolotin

(10) Patent No.: US 9,282,954 B2
(45) Date of Patent: Mar. 15, 2016

(54) SURGICAL TECHNIQUES AND CLOSURE DEVICES FOR DIRECT CARDIAC CATHETERIZATION

(75) Inventor: Gil Bolotin, Zikhron Yakov (IL)

(73) Assignee: RAMBAM HEALTH CORPORATION, Haifa (IL)

( * ) Notice: Subject to any disclaimer, the term of this patent is extended or adjusted under 35 U.S.C. 154(b) by 833 days.

(21) Appl. No.: 13/391,291

(22) PCT Filed: Aug. 18, 2010

(86) PCT No.: PCT/IB2010/053725
§ 371 (c)(1),
(2), (4) Date: Feb. 20, 2012

(87) PCT Pub. No.: WO2011/021158
PCT Pub. Date: Feb. 24, 2011

(65) Prior Publication Data
US 2012/0150224 A1 Jun. 14, 2012

Related U.S. Application Data

(60) Provisional application No. 61/234,691, filed on Aug. 18, 2009.

(51) Int. Cl.
*A61B 17/00* (2006.01)
*A61B 17/34* (2006.01)
(Continued)

(52) U.S. Cl.
CPC ......... *A61B 17/0057* (2013.01); *A61B 17/3421* (2013.01); *A61B 17/3415* (2013.01);
(Continued)

(58) Field of Classification Search
CPC ............... A61B 17/0057; A61B 17/04; A61B 17/3421; A61B 17/3415; A61B 17/0644; A61B 17/12013; A61B 17/068; A61B 2017/00243; A61B 2017/306; A61B 2017/00668; A61B 2017/00867; A61B 2017/0641; A61B 2017/0645; A61B 2017/00637; A61B 2017/00862; A61B 2017/00592; A61B 2017/00584; A61B 2017/00579

USPC ......... 606/232, 138–141, 151, 155–158, 213, 606/75, 219, 323, 326, 108, 192, 198, 194, 606/215, 216, 221, 142; 623/1.15, 1.16, 623/1.18–1.21, 1.26, 2.1, 2.14, 2.17–2.18, 623/1.36
See application file for complete search history.

(56) References Cited

U.S. PATENT DOCUMENTS 4,723,940 A 2/1988 Wiegerinck
5,685,856 A 11/1997 Lehrer
(Continued)

FOREIGN PATENT DOCUMENTS

WO 2008/044147 A2 4/2008

OTHER PUBLICATIONS

Semple T et al., "Left Heart Catheterization by Direct Ventricular Puncture," Brit. Heart J., 1968, 30, 402.
(Continued)

*Primary Examiner* — Jocelin Tanner
(74) *Attorney, Agent, or Firm* — Symbus Law Group, LLC; Clifford D. Hyra

(57) ABSTRACT

A surgical closure device (100) includes (a) a continuous loop (110), which defines an opening (112) therethrough, and which is configured to assume at least an open shape and a closed shape, and (b) four or more tissue anchors (130), coupled to the loop (110). An area of the opening (112) when the loop (110) assumes the closed shape is less than 80% of the area of the opening (112) when the loop (110) assumes the open shape. The loop (110) is configured such that, as the loop (110) transitions from the open shape to the closed shape, all of the anchors (130) move in generally radial directions, and do not move in generally circumferential directions; and a first set of two or more of the anchors (130A) move on average a first distance, and a second set of two or more of the anchors (130B) move on average a second distance that is between 40% and 80% of the first distance.

10 Claims, 15 Drawing Sheets

(51) Int. Cl.
 *A61B 17/064* (2006.01)
 *A61B 17/30* (2006.01)

(52) U.S. Cl.
 CPC ............... *A61B2017/00243* (2013.01); *A61B 2017/00637* (2013.01); *A61B 2017/00668* (2013.01); *A61B 2017/00867* (2013.01); *A61B 2017/0641* (2013.01); *A61B 2017/0645* (2013.01); *A61B 2017/306* (2013.01); *A61B 2017/3425* (2013.01)

(56) References Cited

U.S. PATENT DOCUMENTS

| | | | |
|---|---|---|---|
| 5,865,809 | A | 2/1999 | Moenning et al. |
| 6,001,110 | A * | 12/1999 | Adams ................ 606/151 |
| 6,080,175 | A | 6/2000 | Hogendijk |
| 6,193,734 | B1 | 2/2001 | Bolduc et al. |
| 6,338,710 | B1 | 1/2002 | Takahashi et al. |
| 6,786,898 | B2 | 9/2004 | Guenst |
| 7,022,131 | B1 | 4/2006 | Derowe et al. |
| 7,063,711 | B1 | 6/2006 | Loshakove et al. |
| 7,146,225 | B2 | 12/2006 | Guenst et al. |
| 7,189,201 | B2 | 3/2007 | Borst et al. |
| 7,338,441 | B2 | 3/2008 | Houser et al. |
| 7,534,260 | B2 | 5/2009 | Lattouf |
| 2003/0093096 | A1 | 5/2003 | McGuckin et al. |
| 2004/0039414 | A1 * | 2/2004 | Carley et al. ........... 606/213 |
| 2004/0138522 | A1 | 7/2004 | Haarstad et al. |
| 2005/0234508 | A1 * | 10/2005 | Cummins et al. ....... 606/213 |
| 2005/0273129 | A1 | 12/2005 | Michels et al. |
| 2005/0283188 | A1 * | 12/2005 | Loshakove et al. ..... 606/213 |
| 2006/0241544 | A1 | 10/2006 | Haverich |
| 2006/0247672 | A1 | 11/2006 | Vidlund et al. |
| 2007/0049952 | A1 | 3/2007 | Weiss |
| 2007/0198057 | A1 * | 8/2007 | Gelbart et al. .......... 606/213 |
| 2008/0306333 | A1 | 12/2008 | Chin |
| 2008/0306491 | A1 * | 12/2008 | Cohen et al. ........... 606/142 |
| 2009/0082620 | A1 | 3/2009 | Haarstad et al. |
| 2009/0143808 | A1 * | 6/2009 | Houser .................. 606/170 |
| 2010/0228269 | A1 * | 9/2010 | Garrison et al. ........ 606/139 |

OTHER PUBLICATIONS

Featherstone et al., "Improving the speed of shape memory alloy actuators by faster electrical heating," In Proceedings of the Ninth International Symposium on Experimental Robotics, Paper ID 128 (2004).
Roubicek et al, "Thermodynamics of shape-memory alloys under electric current," Zeitschrift fur Angewandte Mathematik und Physik (ZAMP) (Jun. 2009).
Search report and IPER for parent PCT Application No. PCT/IB2010/053725, mailed on Feb. 21, 2012.
Walther et al.,"The Annals of Thoracic Surgery," (2009), 87:276-283.
Lichtenstein et al, "Transapical Transcatheter Aortic Valve Implantation in Humans : Initial Clinical Experience," (2006), 114:591-596.

* cited by examiner

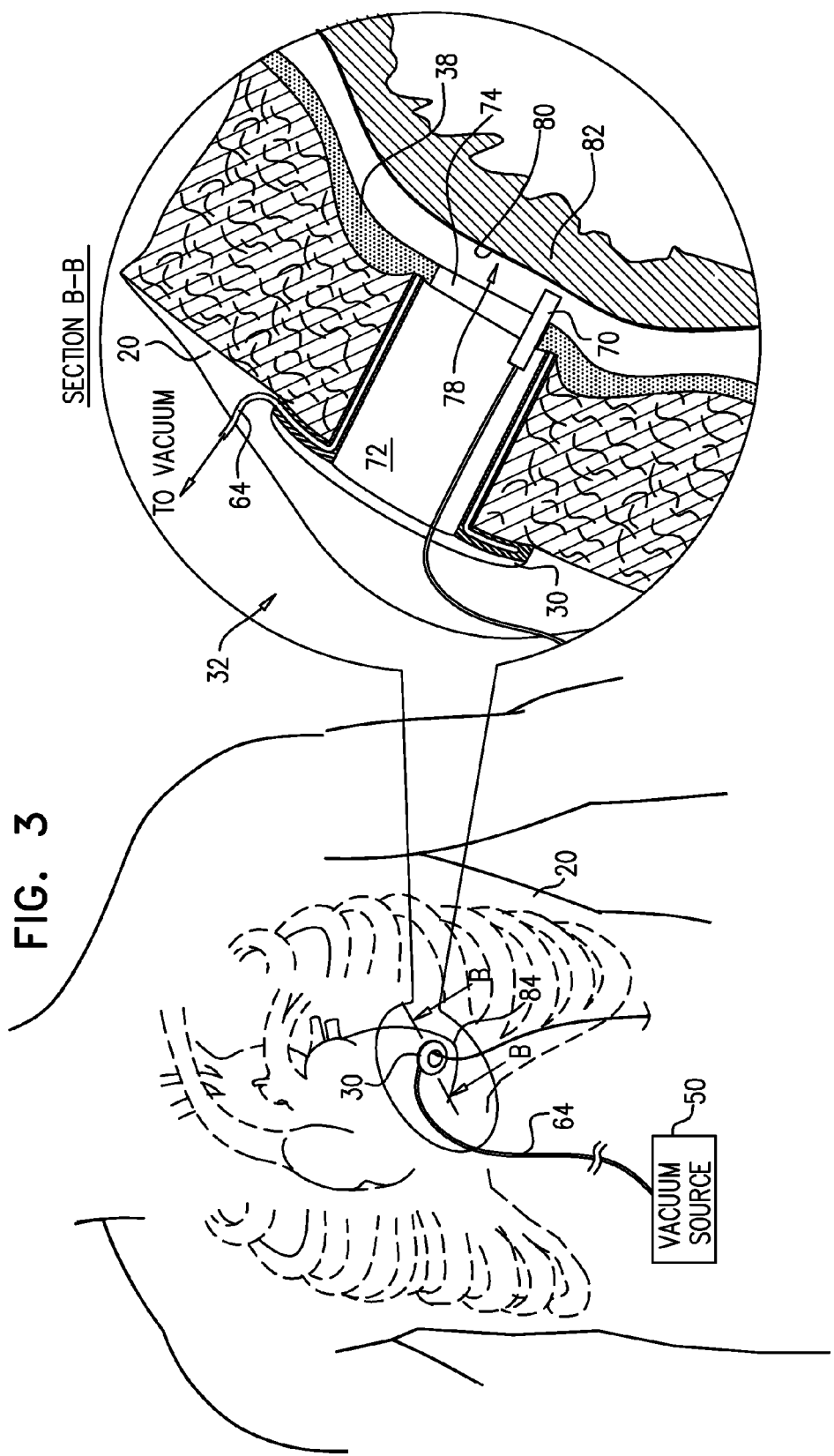

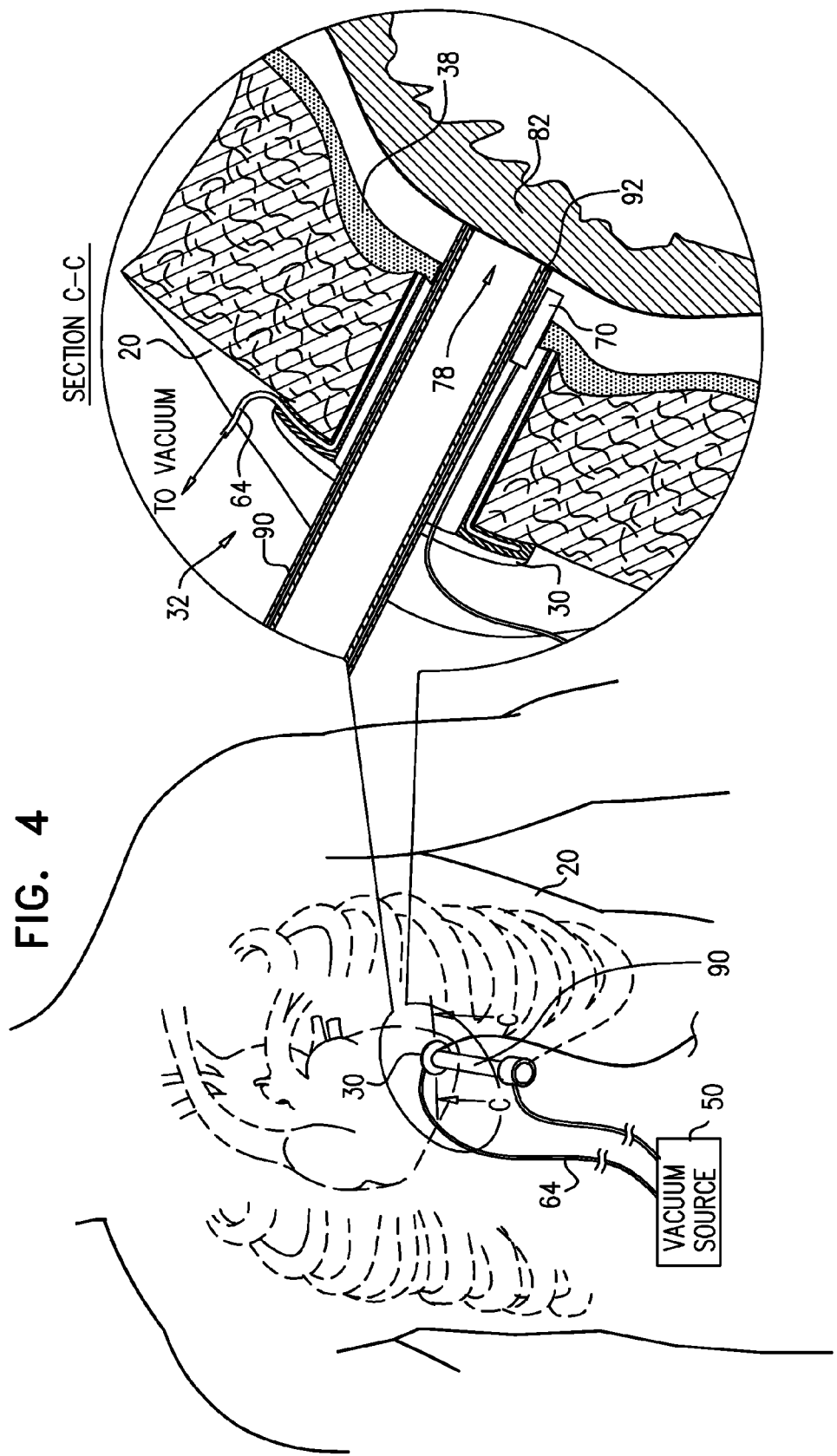

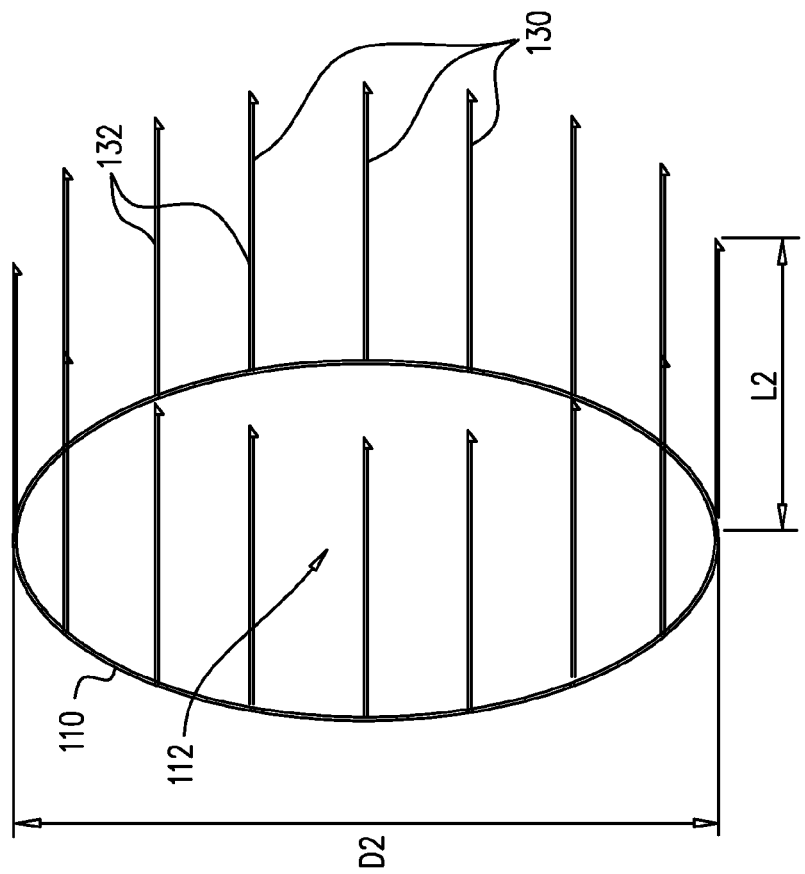
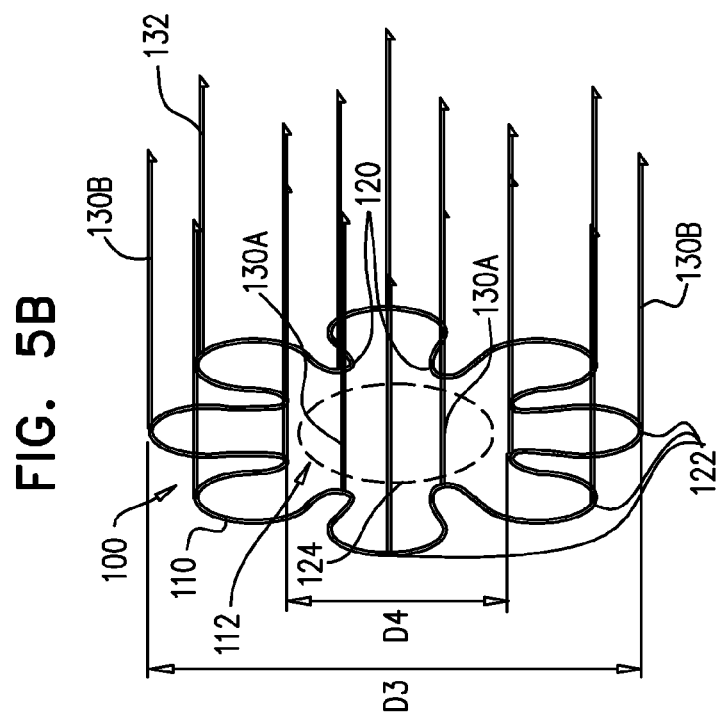

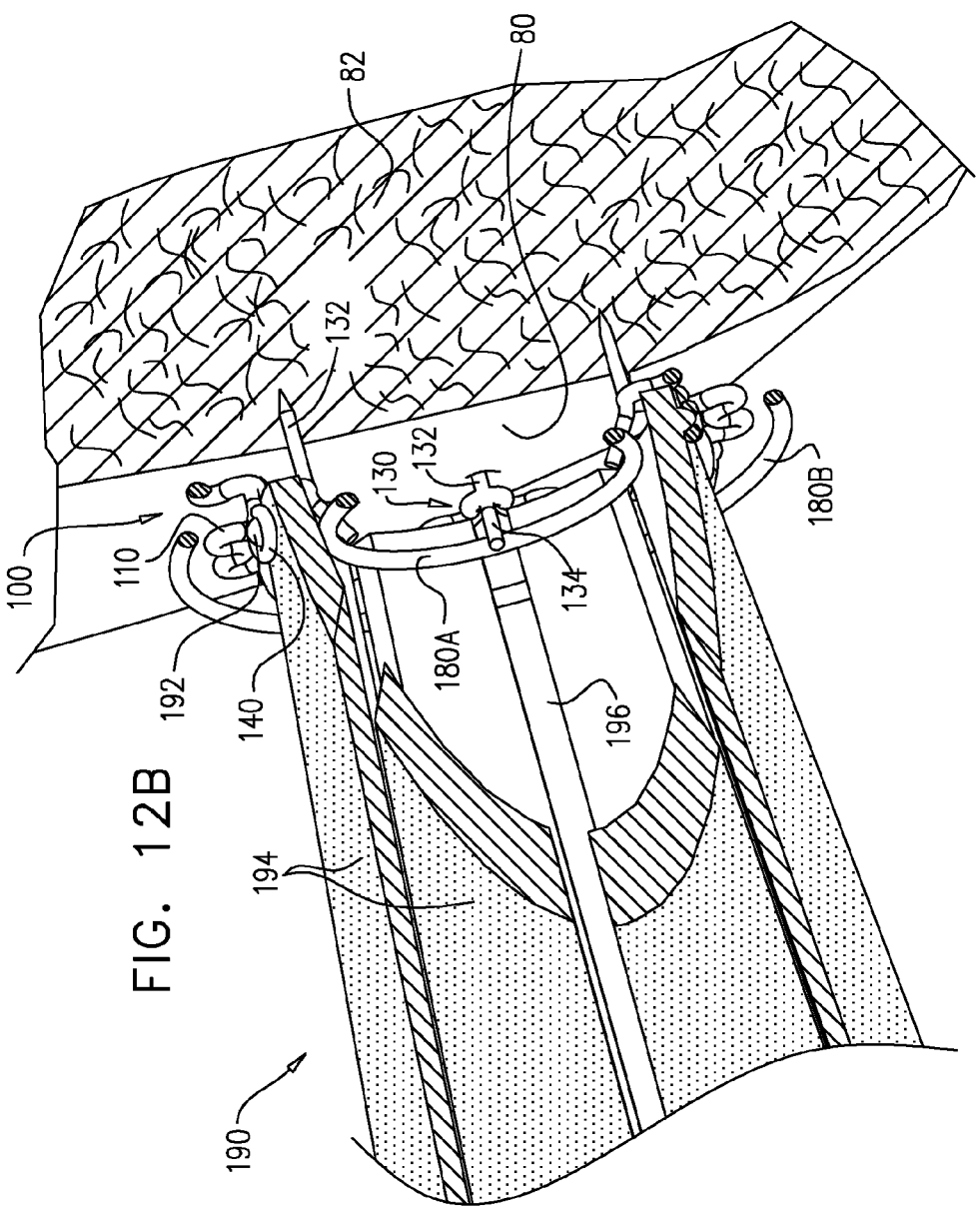

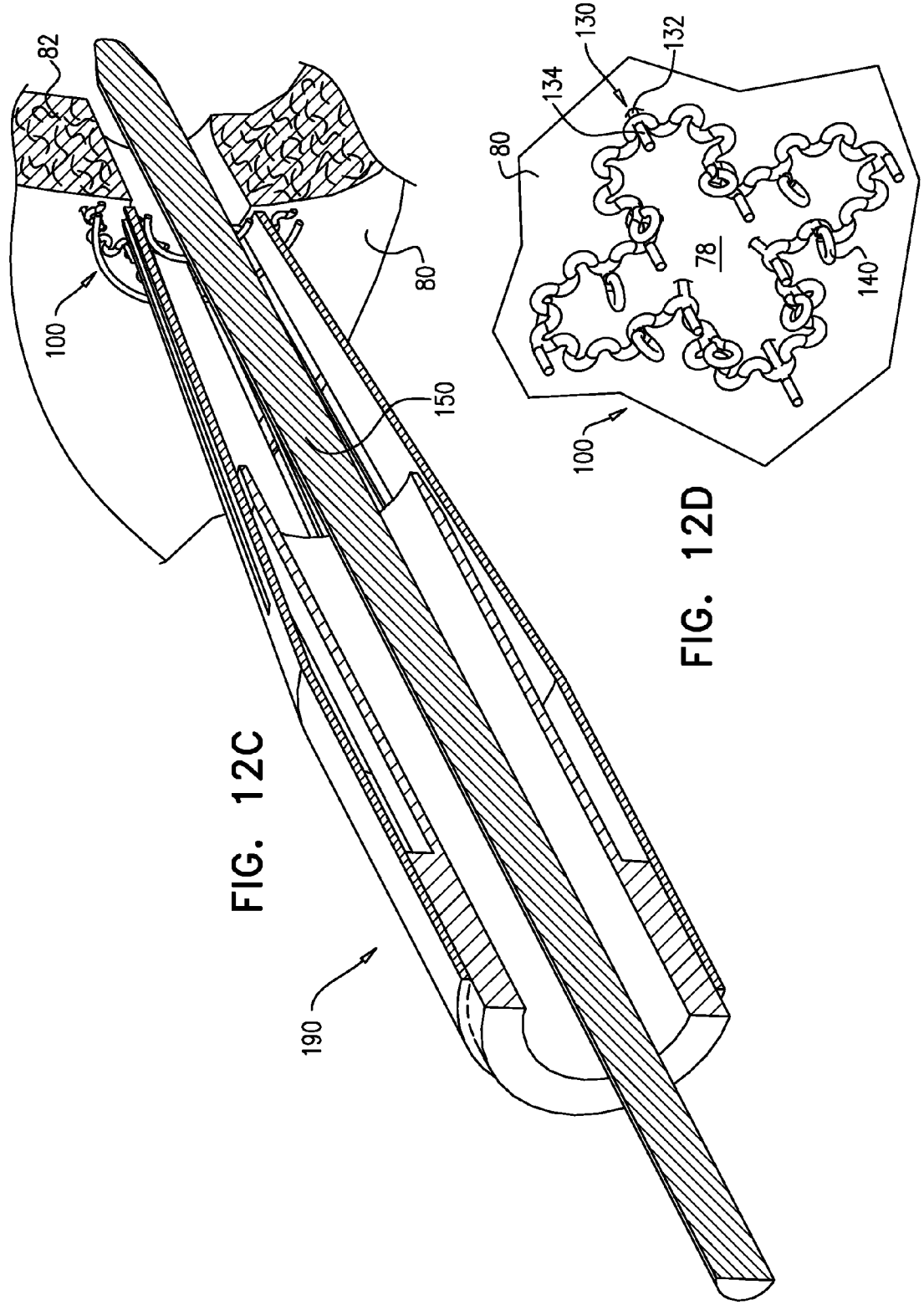

SURGICAL TECHNIQUES AND CLOSURE DEVICES FOR DIRECT CARDIAC CATHETERIZATION

CROSS-REFERENCE TO RELATED APPLICATIONS

This application is the U.S. national phase application of PCT International Application No. PCT/IB2010/053725 filed on 18 Aug. 2010, which claims the benefit of U.S. Provisional Application Ser. No. 61/234,691, filed on 18 Aug. 2009, all of which are hereby incorporated by reference in their entirety.

CROSS-REFERENCE TO RELATED APPLICATIONS

The present application claims priority from U.S. Provisional Application 61/234,691, filed Aug. 18, 2009, entitled, "Surgical techniques and closure devices for direct cardiac catheterization," which is assigned to the assignee of the present application and is incorporated herein by reference.

FIELD OF THE APPLICATION

The present invention relates generally to cardiac surgical methods and devices, and specifically to minimally-invasive surgical tools and methods for performing transapical surgical procedures.

BACKGROUND OF THE APPLICATION

Various cardiac medical procedures are performed using transapical delivery of medical devices to the left or right ventricle. The ventricle is accessed directly through a passage formed through the myocardium near the apex of ventricle. Such medical procedures include valve replacement, such as aortic or mitral valve replacement, and valve repair, such as mitral valve repair. Conventional transapical delivery procedures typically are performed under general anesthesia, and include performing a small thoracotomy, spreading the ribs using a mechanical retractor, opening of the pericardial sac, suturing the hole made through the ventricle, and closing the thoracotomy.

U.S. Pat. No. 7,060,084 to Loshakove et al., which is incorporated herein by reference, describes a device for sealing a hole in a blood vessel, comprising a ring; a plurality of spikes extending from said ring towards a center of said ring, and to first direction along an axis of said ring, said spikes being adapted for engaging a blood vessel; and a plurality of tabs extending substantially radially from said ring. Rotating said tabs around said ring distorts said ring such that said spikes are rotated in a same direction as said tabs.

US Patent Application Publication 2005/0273129 to Michels et al., which is incorporated herein by reference, describes medical techniques for accessing an anatomical space of the body and particularly for penetrating the epicardium to access pericardial space and the epicardial surface of the heart in a minimally invasive manner employing suction. The distal end of a tubular access sleeve having a sleeve wall surrounding a sleeve access lumen and extending between a sleeve proximal end and a sleeve distal end having a plurality of suction ports arrayed around the sleeve access lumen distal end opening is applied against an outer tissue layer. Suction is applied through the plurality of suction ports to a plurality of portions of the outer tissue layer. A perforation instrument is introduced through the sleeve access lumen to perforate the outer tissue layer to form an access perforation into the anatomic space while the applied suction stabilizes the outer tissue layer, whereby further treatment drugs and devices can be introduced into the anatomic space.

PCT Publication WO 2008/044147 to Chatel, which is incorporated herein by reference, describes a device for the implantation of an apparatus on or in a mammalian internal organ, comprising: a tube for passing the apparatus through, one end of which is intended to be applied to a site chosen for the implantation of the apparatus, and the other end of which is intended to emerge outside the body of the mammal; fixing means suitable for fixing the device on the organ and for applying the end of the tube to the chosen site, said means being controlled from outside the body; and rigidifying means suitable for rigidifying the device, said means being controlled from outside the body, so as to fix the position of the tube relative to the fixing means and to the organ, once the device has been fixed on the organ and the end of the tube has been applied to the chosen site by the fixing means.

US Patent Application Publication 2007/0049952 to Weiss, which is incorporated herein by reference, describes a method and apparatus for repairing the heart's mitral valve by using anatomic restoration without the need to stop the heart, use a heart-lung machine or making incisions on the heart. The method involves inserting a leaflet clamp through the heart's papillary muscle from which the leaflet has been disconnected, clamping the leaflet's free end and then puncturing the leaflet. One end of a suture is then passed through the hollow portion of the clamp, while the other end of the suture is maintained external to the heart. The clamp is then removed and the suture's two ends are fastened together with a securement ring/locking cap assembly to the heart wall exterior, thereby reconnecting the leaflet to the corresponding papillary muscle. The introduction of the clamp, puncturing of the leaflet, passage of the suture therethrough and removal of the clamp can be conducted a plurality of times before each suture's two ends are fastened to the securement ring/locking cap assembly.

US Patent Application Publication 2008/0306333 to Chin, which is incorporated herein by reference, describes apparatus and method for performing surgical procedures within the mediastinum and within the pericardium include an endoscopic cannula having a transparent tip, and an endoscope for introduction into the mediastinum and optionally into the pericardium via a single subxiphoid incision. A cavity may be initially dilated for advancing the endoscopic cannula using a dilating tool that exerts a lateral-expansive force against surrounding tissue for evaluating the endoscopic cannula to be introduced into the mediastinum. Other surgical instruments are positioned through the endoscopic cannula to cut a flap of the pericardium as an opening through which other surgical apparatus may be introduced. The endoscopic cannula may be swept around selected regions of the heart through an aperture near the apex of the heart to facilitate placement of epicardial tacks about regions of the heart.

Semple T et al., in an article entitled, "Left Heart Catheterization by Direct Ventricular Puncture," Brit. Heart J., 1968, 30, 402, which is incorporated herein by reference, describe a method of obtaining pressure gradient readings across the aortic and mitral valves by the use of a needle-type Teflon catheter introduced to the ventricle directly through the chest wall at the cardiac apex. After evaluating the method in dogs, the authors employed the method in a pilot study of 55 patients.

Medtronic, Inc. manufactures the Octopus® family of tissue stabilizers, which are reusable tissue stabilizers with collapsible suction pods that enable insertion into and removal from the thoracic cavity through a port, thus eliminating the need for an incision for insertion of the stabilizer.

The following publications, all of which are incorporated herein by reference, may be of interest:

U.S. Pat. No. 4,723,940 to Wiegerinck
U.S. Pat. No. 5,685,856 to Lehrer
U.S. Pat. No. 5,865,809 to Moenning et al.
U.S. Pat. No. 6,080,175 to Hogendijk
U.S. Pat. No. 6,338,710 to Takahashi et al.
U.S. Pat. No. 6,786,898 to Guenst
U.S. Pat. No. 7,146,225 to Guenst et al.
U.S. Pat. No. 7,189,201 to Borst et al.
U.S. Pat. No. 7,338,441 to Houser et al.
U.S. Pat. No. 7,534,260 to Lattouf
US Patent Application Publication 2004/0138522 to Haarstad et al.
US Patent Application Publication 2006/0241544 to Haverich
US Patent Application Publication 2006/0247672 to Vidlund et al.
US Patent Application Publication 2009/0082620 to Haarstad et al.

Shape memory alloys are a group of materials that, after being deformed, return to a predetermined shape when heated. This memory effect is caused by a temperature-dependent crystal structure. One-way shape memory alloys remember a single shape, to which they return upon being heated. Two-way shape memory alloys remember two different shapes, the first at a relatively low temperature, and the second at a higher temperature.

The following references, all of which are incorporated herein by reference, may be of interest:

Featherstone et al., "Improving the speed of shape memory alloy actuators by faster electrical heating," In Proceedings of the Ninth International Symposium on Experimental Robotics, Paper ID 128 (2004)

Roubíček et al., "Thermodynamics of shape-memory alloys under electric current," Zeitschrift für Angewandte Mathematik and Physik (ZAMP) (June 2009)

SUMMARY OF APPLICATIONS

In some embodiments of the present invention, a surgical closure device comprises a continuous loop, which is configured to assume at least open and closed shapes. The closure device further comprises a plurality of tissue anchors coupled to the loop. During a cardiac medical procedure, a surgeon couples the closure device to an external surface of the myocardium, by inserting anchoring portions of the anchors into tissue of the myocardium while the loop is in the open shape. The surgeon punctures the myocardium through the loop to form a passage through the myocardium, and inserts a catheter into the heart via the loop and the passage. After performing a medical procedure on the heart via the catheter, the surgeon withdraws the catheter from the heart. The surgeon causes the loop to assume the closed shape. Assumption of the closed shape draws the anchors toward a central region of the loop, thereby squeezing together the cardiac tissue of the myocardium surrounding the passage made through the myocardium, and closing the passage.

For some applications, when the closure device assumes the closed shape, the loop is shaped so as to define: (a) two or more inwardly-extending portions, which extend toward a central region of the loop, and (b) two or more outwardly-extending portions, which extend away from the central region. The inwardly-extending portions alternate with the outwardly-extending portions around the loop. The closed shape thus may be similar to the shape of an asterisk or a flower. The tissue anchors are coupled to the loop such that when the loop assumes the closed shape, a first set of two or more of the tissue anchors are coupled to respective ones of the inwardly-extending portions, and a second set of two or more of the tissue anchors are coupled to respective ones of the outwardly-extending portions. Typically, an area of the opening when the loop assumes the closed shape is less than 80% of the area of the opening when the loop assumes the open shape.

Typically, the loop is configured such that, as the loop transitions from the open shape to the closed shape, all of the anchors move in generally radial directions, and do not move in generally circumferential directions. Such radial motion is less likely to tear or otherwise damage the tissue of the myocardium than is circumferential motion. The hearts of older patients, upon whom cardiac procedures are most commonly performed, are particularly vulnerable to such tearing.

The loop is typically configured such that, as the loop transitions from the open shape to the closed shape, the anchors of the first, inner set move a greater distance than the anchors of the second, outer set. Movement by these two distances has the effect of applying two strengths of closure on the heart muscle: an inner, greater level of closure, surrounded by an outer, lesser level of closure. Together, the two levels of closure together tightly close the passage made through the myocardium, while minimizing the risk of damaging heart tissue.

For some applications, the anchors are configured to transition from respective initial angular orientations to respective tissue-locking angular orientations, in which each of the anchoring portions defines an angle of between 45 and 75 degrees, e.g., between 55 and 65 degrees, such as 60 degrees, with the plane defined by the opening of the loop. This angle of the anchoring portions helps lock the anchors to the cardiac tissue. In addition, when the loop assumes the closed shape, the angling of the anchoring portions increases the inwardly-directed pressure applied by the closure device to the cardiac tissue, thereby helping close the puncture through the heart wall.

Because of these characteristics, the closure device is particularly suitable for application to cardiac tissue. In contrast, the inventor believes that closure devices designed for coupling to blood vessels, such as described in some of the above-mentioned references, are not generally well-suited for application to cardiac tissue. For example, such blood vessel closure devices, if applied to cardiac tissue, would generally not adequately grip the tissue, and might have a tendency to tear the tissue if they apply circumferential force. In addition, the motion of the myocardium may cause the closure device to slowly slip out of the cardiac tissue, since it is not suitably anchored (arterial walls move less and in a more orderly fashion than the myocardium).

In some applications of the present invention, a surgical system and procedure are provided for performing a transapical surgical procedure. For some applications, the procedure uses the closure device described hereinabove, while for other applications, other closure techniques are used.

For some applications, the surgical system comprises at least one vacuum source, an outer tubular tool, and an inner tubular tool. The outer tubular tool is shaped so as to define one or more outer-tool suction ports, which are arranged around a distal end of the outer tubular tool, and which are in fluid communication with the vacuum source. The inner tubular tool is sized to pass through the outer tubular tool, and is shaped so as to define one or more inner-tool suction ports, which are arranged around a distal end of the inner tubular tool, and which are in fluid communication with the vacuum source. For some applications, the surgical system further comprises an imaging probe. The imaging probe and outer and inner tubular tools are sized to allow the imaging probe to pass through the outer tubular tool between the outer and inner tubular tools.

During a surgical procedure using the surgical system, a surgeon passes the outer tubular tool through a chest wall of a subject, and advances the outer tubular tool to a site on an outer surface of a pericardium. The surgeon applies suction to the outer surface of the pericardium through the outer-tool suction ports arranged around the distal end of the outer tubular tool. The surgeon introduces a first penetration tool through a lumen of the outer tubular tool, and uses the first penetration tool to puncture the pericardium to form a first passage therethrough. The surgeon then withdraws the first penetration tool from the lumen of the outer tubular tool.

The surgeon passes the inner tubular tool through the lumen of the outer tubular tool and through the first passage through the pericardium, to a site on an outer surface of a myocardium. The surgeon applies suction to the outer surface of the myocardium through the inner-tool suction ports arranged around the distal end of the inner tubular tool. The surgeon introduces a second penetration tool through a lumen of the inner tubular tool, and uses the second penetration tool to puncture the myocardium to form a second passage therethrough. The surgeon introduces a medical device into a heart chamber via the second passage.

For applications in which the closure device described above is used during the surgical procedure, after applying suction to the outer surface of the myocardium, the surgeon passes the closure device through the inner tubular tool, and couples the closure device to the outer surface of the myocardium while the closure device is in its open shape. The surgeon passes the second penetration tool through the opening of the open closure device, and punctures the myocardium. After performing the medical procedure on the heart, the surgeon causes the closure device to assume its closed shape.

For some applications, the surgical method includes, before applying the suction through the inner-tool suction ports, passing an imaging probe through the lumen of the outer tubular tool, and using the imaging probe to locate the site on the outer surface of the myocardium.

The above-mentioned tools and procedures advantageously enable minimally invasive access to the ventricles, and, via the ventricles, to the atria, aorta, and pulmonary blood vessels. The procedures generally do not require spreading of the patient's ribs, general anesthesia, mechanical ventilation, or the performance of an open thoracotomy. The procedures thus generally reduce patient pain during and after surgery, and minimize the likelihood of complications.

There is therefore provided, in accordance with an application of the present invention, apparatus including a surgical closure device, which includes:

a continuous loop, which defines an opening therethrough, and which is configured to assume at least an open shape and a closed shape, wherein an area of the opening when the loop assumes the closed shape is less than 80% of the area of the opening when the loop assumes the open shape; and four or more tissue anchors, which are coupled to the loop, wherein the loop is configured such that, as the loop transitions from the open shape to the closed shape:
all of the anchors move in generally radial directions, and do not move in generally circumferential directions, and
a first set of two or more of the anchors move on average a first distance, and a second set of two or more of the anchors move on average a second distance that is between 40% and 80% of the first distance.

For some applications, the first distance is between 4 and 10 mm.

For some applications, the loop is configured such that the area of the opening is between 28 and 314 mm2 when the loop assumes the open shape. Alternatively, the loop is configured such that the area of the opening is between 10 and 565 mm2 when the loop assumes the open shape.

For some applications, the loop includes a metal. For some applications, the metal includes stainless steel. For some applications, the metal is non-elastic. For some applications, the metal includes a shape memory alloy. For some applications, the shape memory alloy of the loop is configured to cause the loop to transition from the open shape to the closed shape responsively to application of an electrical current to the alloy.

For any of the applications described above, the closure device may be configured such that when the anchors assume respective initial angular orientations, the anchoring portions define respective angles of between 75 and 115 degrees with a plane defined by the opening. For some applications, the closure device is configured such that when the anchors assume respective tissue-locking angular orientations, the angles are between 45 and 75 degrees. For some applications, the apparatus further includes a tool, which is configured to be removably coupled to the closure device and subsequently decoupled therefrom, which tool is configured to perform one or both actions selected from the group consisting of: transitioning the loop from the open shape to the closed shape, transitioning the loop from the closed shape to the open shape, transitioning the tissue anchors from the initial angular orientations to the tissue-locking angular orientations, and transitioning the tissue anchors from the tissue-locking angular orientations to the initial angular orientations.

For any of the applications described above, the apparatus may further include a tool, which is configured to be removably coupled to the closure device and subsequently decoupled therefrom, which tool is configured to perform one or more actions selected from the group consisting of: transitioning the loop from the open shape to the closed shape, and transitioning the loop from the closed shape to the open shape.

There is further provided, in accordance with an application of the present invention, apparatus including a surgical closure device, which includes:

a continuous loop, which defines an opening therethrough, and which is configured to assume at least an open shape and a closed shape, wherein an area of the opening when the loop assumes the closed shape is less than 80% of the area of the opening when the loop assumes the open shape; and four or more tissue anchors, which are coupled to the loop, and which are shaped so as to define respective anchoring portions, wherein the closure device is configured such that (a) when the anchors assume respective initial angular orientations, the anchoring portions define respective angles of between 75 and 115 degrees with a plane defined by the opening, and (b) when the anchors assume respective tissue-locking angular orientations, the respective angles are between 45 and 75 degrees.

For some applications, when the loop assumes the closed shape, the loop is shaped so as to define: (a) two or more inwardly-extending portions, which extend toward a central region of the loop, and (b) two or more outwardly-extending portions, which extend away from the central region, and the inwardly-extending portions alternate with the outwardly-extending portions around the loop.

For some applications, the loop is configured such that the area of the opening is between 28 and 314 mm2 when the loop assumes the open shape. Alternatively, the loop is configured such that the area of the opening is between 10 and 565 mm2 when the loop assumes the open shape.

For some applications, the closure device is configured such that the angles are between 55 and 65 degrees, when the anchors assume the tissue-locking angular orientations.

For some applications, the anchors are configured to assume the respective initial angular orientations when constrained, and the respective tissue-locking angular orientations when unconstrained.

For some applications, when the anchors assume the respective tissue-locking angular orientations, each of the anchoring portions extends from the loop toward an axis of the closure device that (a) is perpendicular to the plane defined by the opening and (b) passes through a central region of the loop.

For any of the applications described above, the anchoring portions may extend from the loop into a first space on a first side of the plane defined by the opening; the anchors may be shaped so as to further define respective non-anchoring alignment portions, which extend from the loop into a second space on a second side of the plane; and the anchors may be configured such that changing of angles of the alignment portions with respect to the plane causes associated changes of the angles of the respective anchoring portions with respect to the plane.

For some applications, the anchors are configured to assume the respective initial angular orientations when constrained, and the respective tissue-locking orientations when unconstrained, and the apparatus further includes one or more constraining members, which, when initially removably coupled to alignment portions, constrain the anchors to assume the initial angular orientations, and when subsequently removed from the alignment portions, allow the anchors to assume the tissue-locking orientations. For some applications, the one or more constraining members include one or more rings.

For any of the applications described above, the loop may be configured such that, as the loop transitions from the open shape to the closed shape, all of the anchors move in generally radial directions, and do not move in generally circumferential directions.

For any of the applications described above, the apparatus may further include a tool, which is configured to be removably coupled to the closure device and subsequently decoupled therefrom, which tool is configured to perform one or more actions selected from the group consisting of: transitioning the loop from the open shape to the closed shape, transitioning the loop from the closed shape to the open shape, transitioning the tissue anchors from the initial angular orientations to the tissue-locking angular orientations, and transitioning the tissue anchors from the tissue-locking angular orientations to the initial angular orientations.

There is still further provided, in accordance with an application of the present invention, apparatus including a surgical closure device, which includes:
a continuous loop, which defines an opening therethrough, and which is configured to assume at least:
an open shape, and
a closed shape, in which the loop is shaped so as to define:
(a) two or more inwardly-extending portions, which extend toward a central region of the loop, and (b) two or more outwardly-extending portions, which extend away from the central region, wherein the inwardly-extending portions alternate with the outwardly-extending portions around the loop,
wherein an area of the opening when the loop assumes the closed shape is less than 80% of the area of the opening when the loop assumes the open shape; and four or more tissue anchors, which are coupled to the loop such that when the loop assumes the closed shape, a first set of two or more of the tissue anchors are coupled to respective ones of the inwardly-extending portions, and a second set of two or more of the tissue anchors are coupled to respective ones of the outwardly-extending portions.

For some applications, the loop is configured such that, as the loop transitions from the open shape to the closed shape, all of the anchors move in generally radial directions, and do not move in generally circumferential directions.

For some applications, the loop is configured such that the area of the opening is between 28 and 314 mm2 when the loop assumes the open shape. Alternatively, the loop is configured such that the area of the opening is between 10 and 565 mm2 when the loop assumes the open shape.

For some applications, the loop is configured to assume a partially closed shape having a partially closed-shape area that is greater than the area of the opening when the loop assumes the closed shape, and less than the area of the opening when the loop assumes the open shape.

For some applications, the open shape is selected from the group of shapes consisting of: a circle, an ellipse, a square, and a polygon. For some applications, when the loop assumes the open shape, the loop is shaped so as to define the inwardly-extending portions, which extend a lesser distance toward a center of the loop than when the loop assumes the closed shape.

For some applications, the inwardly-extending and outwardly-extending portions of the loop are wavy, both when the loop assumes the open shape and when the loop assumes the closed shape. For some applications, the anchoring portions are straight. For some applications, at least a portion of the tissue anchors are shaped to define respective barbs.

For some applications, the loop is configured to assume the closed shape when unconstrained. For some applications, the apparatus further includes a tool that is configured to initially constrain the loop in the open shape.

For some applications, the loop includes a metal. For some applications, the metal includes stainless steel. For some applications, the metal is non-elastic. For some applications, the apparatus further includes a tool that is configured to apply a force to the loop that transitions the loop from the open shape to the closed shape.

For some applications, the metal includes a shape memory alloy. For some applications, the shape memory alloy of the loop is trained to be in the closed shape at least within a temperature range of 36 to 40° C. For some applications, the shape memory alloy is configured to cause the loop to transition from the open shape to the closed shape responsively to application of an electrical current to the alloy.

For any of the applications described above, the tissue anchors may be shaped so as to define respective anchoring portions, and the closure device is configured such that when the anchors assume respective initial angular orientations, the anchoring portions define respective angles of between 75 and 115 degrees with a plane defined by the opening. For some applications, the closure device is configured such that when the anchors assume respective tissue-locking angular orientations, the angles are between 45 and 75 degrees. For some applications, the closure device is configured such that the angles are between 55 and 65 degrees, when the anchors assume the tissue-locking angular orientations. For some applications, the anchors are configured to assume the respective initial angular orientations when constrained, and the respective tissue-locking angular orientations when unconstrained. For some applications, the apparatus further includes a tool, which is configured to be removably coupled to the closure device and subsequently decoupled therefrom, which tool is configured to perform one or more actions selected from the group consisting of: transitioning the loop from the open shape to the closed shape, transitioning the loop from the closed shape to the open shape, transitioning the tissue anchors from the initial angular orientations to the tissue-locking angular orientations, and transitioning the tissue anchors from the tissue-locking angular orientations to the initial angular orientations.

For any of the applications described above, the anchoring portions may extend from the loop into a first space on a first side of a plane defined by the opening; the anchors may be shaped so as to further define respective non-anchoring alignment portions, which extend from the loop into a second space on a second side of the plane; and the anchors may be configured such that changing of angles of the alignment portions with respect to the plane causes associated changes of angles of the respective anchoring portions with respect to the plane. For some applications, the anchors are configured to assume respective initial angular orientations when constrained, and respective tissue-locking orientations when unconstrained, and the apparatus further includes one or more constraining members, which, when initially removably coupled to alignment portions, constrain the anchors to assume the initial angular orientations, and when subsequently removed from the alignment portions, allow the anchors to assume the tissue-locking orientations. For some applications, the one or more constraining members include one or more rings.

For any of the applications described above, the anchoring portions may extend from the loop into a first space on a first side of a plane defined by the opening, and the closure device may further include a plurality of extension members, which are coupled to the loop, and which extend from the loop into a second space on a second side of the plane defined by the opening. For some applications, the extension members are shaped so as to define rings. For some applications, the apparatus further includes a tool, which is configured to apply a radially outwardly directed force against the extension members, thereby holding the loop in the open shape. For some applications, the apparatus further includes a tool, which includes engagement elements that are configured to engage the extension members, thereby coupling the tool to the closure device.

For any of the applications described above, the loop may be configured such that, as the loop transitions from the open shape to the closed shape, the anchors of the first set move on average a first distance, and the anchors of the second set move on average a second distance that is between 40 and 80% of the first distance.

For any of the applications described above, the apparatus may further include a tool, which is configured to be removably coupled to the closure device and subsequently decoupled therefrom, which tool is configured to perform one or more actions selected from the group consisting of: transitioning the loop from the open shape to the closed shape, and transitioning the loop from the closed shape to the open shape.

There is additionally provided, in accordance with an application of the present invention, a method including:

coupling a surgical closure device to a surface of cardiac tissue, using four or more tissue anchors of the closure device, which closure device includes a continuous loop that defines an opening therethrough, wherein coupling includes coupling while the loop assumes an open shape;

forming a passage through the cardiac tissue that is surrounded by the loop; and after coupling, closing the passage by transitioning the loop to a closed shape such that, during the transitioning:
  all of the anchors move in generally radial directions, and do not move in generally circumferential directions, and
  a first set of two or more of the anchors move on average a first distance, and a second set of two or more of the anchors move on average a second distance that is between 40% and 80% of the first distance.

For some applications, transitioning includes transitioning the loop to the closed shape in which an area of the opening is less than 80% of the area of the opening when the loop assumes the open shape.

For some applications, transitioning includes transitioning such that the first distance is between 4 and 6 mm.

For some applications, coupling includes coupling the closure device while the anchors assume respective initial angular orientations, in which the anchoring portions define respective angles of between 75 and 115 degrees with a plane defined by the opening. For some applications, coupling includes locking the closure device to the cardiac tissue by transitioning the anchors to respective tissue-locking angular orientations, in which the angles are between 45 and 75 degrees. For some applications, the method further includes, after locking the closure device, unlocking the closure device by transitioning the anchors back to the respective initial angular orientations. For some applications, the method further includes using a tool, which is configured to be removably coupled to the closure device and subsequently decoupled therefrom, to perform one or both actions selected from the group consisting of: transitioning the loop from the open shape to the closed shape, transitioning the loop from the closed shape to the open shape, transitioning the tissue anchors from the initial angular orientations to the tissue-locking angular orientations, and transitioning the tissue anchors from the tissue-locking angular orientations to the initial angular orientations.

For some applications, the method further includes using a tool, which is configured to be removably coupled to the closure device and subsequently decoupled therefrom, to perform one or more actions selected from the group consisting of: transitioning the loop from the open shape to the closed shape, and transitioning the loop from the closed shape to the open shape.

There is yet additionally provided, in accordance with an application of the present invention, a method including:

coupling, to a surface of cardiac tissue, a surgical closure device, which includes a continuous loop that defines an opening therethrough, wherein coupling includes coupling while the loop assumes an open shape, using respective anchoring portions of four or more tissue anchors of the closure device, while the anchors assume respective initial angular orientations, in which the anchoring portions define respective angles of between 75 and 115 degrees with a plane defined by the opening;

transitioning the anchors to assume respective tissue-locking angular orientations, in which the angles are between 45 and 75 degrees;

forming a passage through the cardiac tissue that is surrounded by the loop; and after coupling, closing the passage by transitioning the loop to a closed shape.

For some applications, transitioning includes transitioning the loop to the closed shape in which an area of the opening is less than 80% of the area of the opening when the loop assumes the open shape.

For some applications, transitioning includes transitioning the loop to the closed shape in which the loop is shaped so as to define: (a) two or more inwardly-extending portions, which extend toward a central region of the loop, and (b) two or more outwardly-extending portions, which extend away from the central region, and the inwardly-extending portions alternate with the outwardly-extending portions around the loop.

For some applications, closing includes closing after coupling and after transitioning the anchors to assume the respective tissue-locking angular orientations. For some applications, the angles are between 55 and 65 degrees, when the anchors assume the tissue-locking angular orientations.

For some applications, the method further includes transitioning the anchors from the respective tissue-locking angular orientations back to the respective initial angular orientations. For some applications, the method further includes, after transitioning the anchors back to the respective initial angular orientations, decoupling the closure device from the cardiac tissue, and recoupling the closure device to the cardiac tissue at a different location.

For some applications, the method further includes, after closing the passage, transitioning the loop back to the open shape.

For some applications, the anchors are configured to assume the respective tissue-locking angular orientations when unconstrained, coupling includes constraining the anchors to assume the respective initial angular orientations, and transitioning includes ceasing constraining the anchors, thereby allowing the anchors to assume the respective tissue-locking angular orientations.

For some applications, the anchoring portions extend from the loop into a first space on a first side of the plane defined by the opening; the anchors are shaped so as to further define respective non-anchoring alignment portions, which extend from the loop into a second space on a second side of the plane; and transitioning includes changing angles of the alignment portions with respect to the plane, thereby causing associated changes of the angles of the respective anchoring portions with respect to the plane. For some applications, the anchors are configured to assume the respective initial angular orientations when constrained, and the respective tissue-locking orientations when unconstrained, and coupling includes:

coupling the closure device to the cardiac tissue while one or more constraining members are removably coupled to the alignment portions, thereby constraining the anchors to assume the initial angular orientations; and locking the closure device to the cardiac tissue by removing the constraining members from the alignment portions, thereby allowing the anchors to assume the tissue-locking orientations.

For some applications, the one or more constraining members are one or more rings, and removing includes removing the one or more rings from the alignment portions.

For some applications, the loop is configured such that, as the loop transitions from the open shape to the closed shape, all of the anchors move in generally radial directions, and do not move in generally circumferential directions.

For some applications, the method further includes using a tool, which is configured to be removably coupled to the closure device and subsequently decoupled therefrom, to perform one or more actions selected from the group consisting of: transitioning the loop from the open shape to the closed shape, transitioning the loop from the closed shape to the open shape, transitioning the tissue anchors from the initial angular orientations to the tissue-locking angular orientations, and transitioning the tissue anchors from the tissue-locking angular orientations to the initial angular orientations.

There is also provided, in accordance with an application of the present invention, a method including:

coupling, to a surface of cardiac tissue, a surgical closure device that includes a continuous loop that defines an opening therethrough, wherein coupling includes coupling while the loop assumes an open shape;

forming a passage through the cardiac tissue that is surrounded by the loop; and after coupling, closing the passage by transitioning the loop to a closed shape, in which the loop is shaped so as to define: (a) two or more inwardly-extending portions, which extend toward a central region of the loop, and (b) two or more outwardly-extending portions, which extend away from the central region, wherein the inwardly-extending portions alternate with the outwardly-extending portions around the loop, wherein coupling includes coupling the closure device to the cardiac tissue using respective anchoring portions of four or more tissue anchors of the closure device, which anchors are coupled to the loop such that when the loop assumes the closed shape, a first set of two or more of the tissue anchors are coupled to respective ones of the inwardly-extending portions, and a second set of two or more of the tissue anchors are coupled to respective ones of the outwardly-extending portions.

For some applications, transitioning includes transitioning the loop to the closed shape in which an area of the opening is less than 80% of the area of the opening when the loop assumes the open shape For some applications, the method further includes, after closing the passage, transitioning the loop back to the open shape.

For some applications, the loop is configured to assume the closed shape when unconstrained, coupling includes constraining the loop to assume the open shape, and transitioning includes ceasing constraining the loop, thereby allowing the loop to assume the closed shape. For some applications, constraining includes using a tool to constrain the loop in the open shape.

For some applications, the loop includes a non-elastic metal, and transitioning includes using a tool to apply a force to the loop that transitions the loop from the open shape to the closed shape.

For some applications, coupling includes coupling the closure device while the anchors assume respective initial angular orientations, in which the anchoring portions define respective angles of between 75 and 115 degrees with a plane defined by the opening. For some applications, coupling includes locking the closure device to the cardiac tissue by transitioning the anchors to respective tissue-locking angular orientations, in which the angles are between 45 and 75 degrees. For some applications, the angles are between 55 and 65 degrees, when the anchors assume the tissue-locking angular orientations. For some applications, the anchors are configured to assume the respective initial angular orientations when constrained, coupling includes constraining the anchors to assume the initial angular orientations, and transitioning includes ceasing constraining the anchors, thereby allowing the anchors to assume the tissue-locking angular orientations.

For some applications, the method further includes, after locking the closure device, unlocking the closure device by transitioning the anchors back to the respective initial angular orientations.

For some applications, the method further includes using a tool, which is configured to be removably coupled to the closure device and subsequently decoupled therefrom, to perform one or more actions selected from the group consisting of: transitioning the loop from the open shape to the closed shape, transitioning the loop from the closed shape to the open shape, transitioning the tissue anchors from the initial angular orientations to the tissue-locking angular orientations, and transitioning the tissue anchors from the tissue-locking angular orientations to the initial angular orientations.

For some applications, the anchoring portions extend from the loop into a first space on a first side of a plane defined by the opening; the anchors are shaped so as to further define respective non-anchoring alignment portions, which extend from the loop into a second space on a second side of the plane; and coupling includes changing angles of the alignment portions with respect to the plane, thereby causing associated changes of angles of the respective anchoring portions with respect to the plane.

For some applications, the anchors are configured to assume respective initial angular orientations when constrained, and respective tissue-locking orientations when unconstrained, and coupling includes:

coupling the closure device to the cardiac tissue while one or more constraining members are removably coupled to alignment portions, thereby constraining the anchors to assume the initial angular orientations; and locking the closure device to the cardiac tissue by removing the constraining members from the alignment portions, thereby allowing the anchors to assume the tissue-locking orientations.

For some applications, the one or more constraining members are one or more rings, and removing includes removing the one or more rings from the alignment portions.

For some applications, the anchoring portions extend from the loop into a first space on a first side of the plane defined by the opening, and the closure device further includes a plurality of extension members, which are coupled to the loop, and which extend from the loop into a second space on a second side of the plane defined by the opening. For some applications, the extension members are shaped so as to define rings.

For some applications, coupling includes using a tool to apply a radially outwardly directed force against the extension members, thereby holding the loop in the open shape, and closing the passage includes ceasing to apply the force, thereby allowing the loop to assume the closed shape.

For some applications, coupling includes using a tool that includes engagement elements that initially engage the extension members, thereby coupling the tool to the closure device.

For some applications, transitioning includes transitioning the loop from the open shape to the closed shape such that all of the anchors move in generally radial directions, and do not move in generally circumferential directions.

For some applications, transitioning includes transitioning the loop transitions from the open shape to the closed shape such that the anchors of the first set move on average a first distance, and the anchors of the second set move on average a second distance that is between 40 and 80% of the first distance.

For some applications, transitioning the loop from the open shape to the closed shape includes:

transitioning the loop from the open shape to a partially closed shape having a partially closed-shape area that is greater than the area of the opening when the loop assumes the closed shape, and less than the area of the opening when the loop assumes the open shape;

while the loop is in the partially closed shape, performing at least a portion of medical procedure; and after performing the at least a portion of the medical procedure, transitioning the loop from the partially closed shape to the closed shape.

For some applications, the open shape is selected from the group of shapes consisting of: a circle, an ellipse, a square, and a polygon. For some applications, when the loop assumes the open shape, the loop is shaped so as to define the inwardly-extending portions, which extend a lesser distance toward a center of the loop than when the loop assumes the closed shape.

For some applications, the inwardly-extending and outwardly-extending portions of the loop are wavy, both when the loop assumes the open shape and when the loop assumes the closed shape. For some applications, the anchoring portions are straight.

For some applications, the method further includes using a tool, which is configured to be removably coupled to the closure device and subsequently decoupled therefrom, to perform one or more actions selected from the group consisting of: transitioning the loop from the open shape to the closed shape, and transitioning the loop from the closed shape to the open shape.

There is further provided, in accordance with an application of the present invention, apparatus including:

at least one vacuum source;

an outer tubular tool, which is shaped so as to define one or more outer-tool suction ports, which are arranged around a distal end of the outer tubular tool, and which are in fluid communication with the at least one vacuum source, wherein the outer tubular tool has a cross-sectional area at the distal end of between 38 and 177 mm2; and an inner tubular tool, which is sized to pass through the outer tubular tool, and which is shaped so as to define one or more inner-tool suction ports, which are arranged around a distal end of the inner tubular tool, and which are in fluid communication with the at least one vacuum source.

For some applications, the apparatus further includes an imaging probe, the imaging probe and outer and inner tubular tools are sized to allow the imaging probe to pass through the outer tubular tool between the outer and inner tubular tools.

There is still further provided, in accordance with an application of the present invention, a method including:

passing an outer tubular tool through a chest wall of a subject, and advancing the outer tubular tool to a site on an outer surface of a pericardium;

applying suction to the outer surface of the pericardium through one or more outer-tool suction ports arranged around a distal end of the outer tubular tool;

introducing a first penetration tool through a lumen of the outer tubular tool, and using the first penetration tool to puncture the pericardium to form a first passage therethrough;

withdrawing the first penetration tool from the lumen of the outer tubular tool;

passing an inner tubular tool through the lumen of the outer tubular tool and through the first passage through the pericardium, to a site on an outer surface of a myocardium;

applying suction to the outer surface of the myocardium through one or more inner-tool suction ports arranged around a distal end of the inner tubular tool;

introducing a second penetration tool through a lumen of the inner tubular tool, and using the second penetration tool to puncture the myocardium to form a second passage therethrough; and introducing a medical device into a heart chamber via the second passage.

For some applications, the method further includes, before applying the suction through the inner-tool suction ports, passing an imaging probe through the lumen of the outer tubular tool, and using the imaging probe to locate the site on the outer surface of the myocardium.

The present invention will be more fully understood from the following detailed description of embodiments thereof, taken together with the drawings, in which:

BRIEF DESCRIPTION OF THE DRAWINGS

FIG. 3 is a schematic illustration of the insertion of an imaging probe through the outer tool of FIGS. 2A-C, in accordance with an application of the present invention;

FIG. 4 is a schematic illustration of the insertion of an inner tubular tool through the outer tool of FIGS. 2A-C, in accordance with an application of the present invention;

FIGS. 5A and 5B are schematic illustrations of a surgical closure device in open and closed shapes, respectively, in accordance with an application of the present invention;

FIGS. 12A-D are schematic illustrations of another surgical tool and another transapical surgical procedure, in accordance with an application of the present invention.

DETAILED DESCRIPTION OF APPLICATIONS

Figure 1:
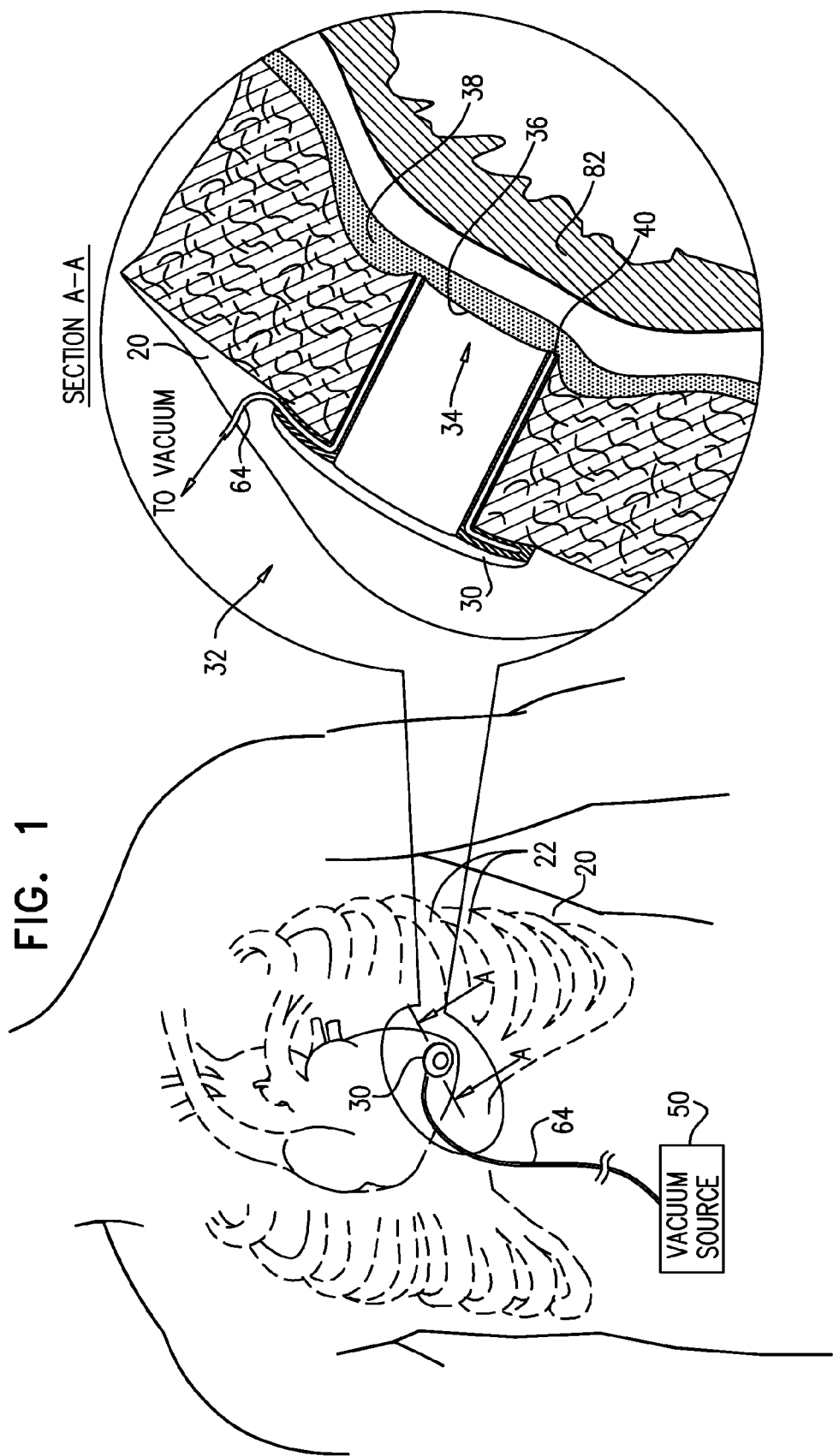
FIG. 1 is a schematic illustration of a first step of a transapical surgical procedure, in accordance with an application of the present invention.

FIG. 1 is a schematic illustration of a first step of a transapical surgical procedure, in accordance with an application of the present invention. The transapical surgical procedure is typically performed to form a passage through the left or right ventricle of a beating heart, near the apex of the ventricle. A catheter is inserted through the passage into the ventricle, and is used to access the heart for performing a medical procedure, such as valve replacement (e.g., aortic or mitral valve replacement), or valve repair (e.g., atrial or mitral valve repair).

A surgeon begins the procedure by making a small incision in a chest wall 20 between two ribs 22, e.g., between the fourth and fifth ribs, or between the fifth and sixth ribs, depending on the location of the apex in the particular patient, typically after administering local anesthesia. The surgeon passes an outer tubular tool 30 of a transapical surgical system 32 through chest wall 20. Typically, the ribs do not need to be spread, because of the small diameter of tool 30. The surgeon advances the tool to a first site 34 on an outer surface 36 of a pericardium 38 of the subject. Typically, a distal end 40 of outer tool 30 is shaped so as to define a sharp cutting surface therearound, such that outer tool 30 serves as a trocar, and is used to cut tissue as the tool is advanced through the chest wall to the pericardium. Alternatively, a separate cutting tool is used either for making the incision in the chest wall and/or for cutting a passage through the tissue, and outer tool 30 is advanced to the pericardium after the separate cutting tool has been removed (configuration not shown).

For some applications, the surgeon uses outer tool 30 to apply suction to outer surface 36 of pericardium 38 from distal end 40 of the tool, in order to tightly hold the pericardium against distal end 40 of tool 30. In order to apply the suction, a vacuum source 50 is coupled to one or more suction channels that pass through the tool and are open through respective outer-tool suction ports at the distal end thereof, such as described immediately hereinbelow with reference to FIGS. 2A-C. Alternatively, for other applications, suction is not applied.

Figure 2A:
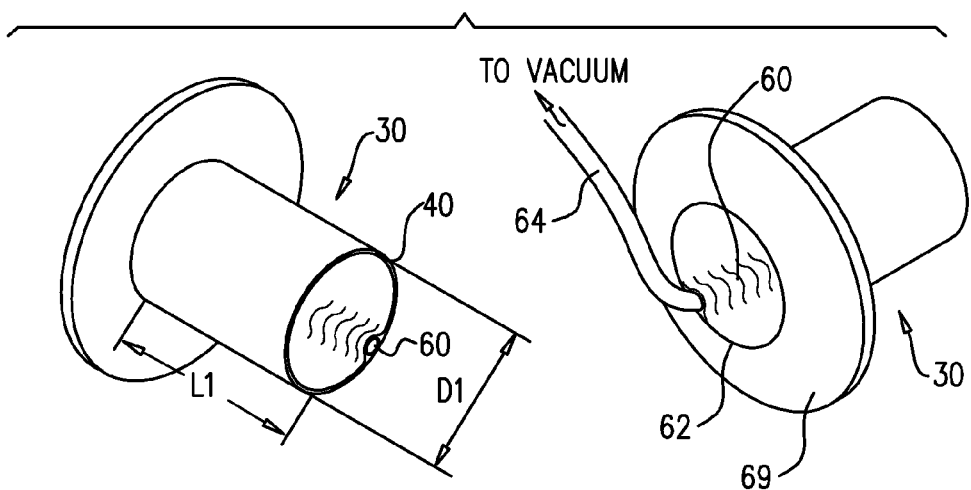
FIGS. 2A-C schematically illustrate several configurations of suction channels through an outer tubular tool using in the surgical procedure of FIG. 1, in accordance with respective applications of the present invention.
Figure 2B:
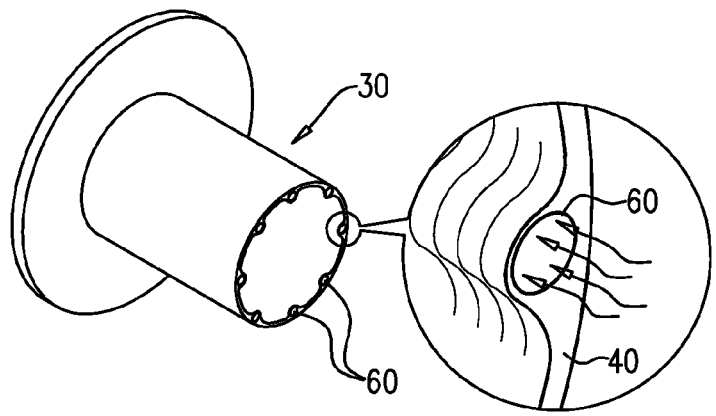
Figure 2C:
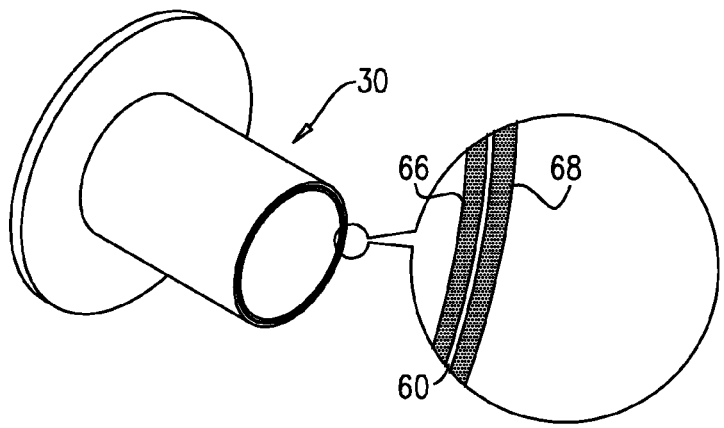

Reference is made to FIGS. 2A-C, which schematically illustrate several configurations of suction channels 60 through outer tool 30, in accordance with respective applications of the present invention. In the configuration shown in FIG. 2A, a wall of outer tool 30 is shaped so as to define a single channel 60 therethrough, along the length of the tool, from a proximal end 62 of the tool to distal end 40 of the tool. Channel 60 may be defined by the wall of the tool, as shown in FIG. 2A, or may be defined by a separate tube coupled to an inner or outer surface of the wall of the tool (configuration not shown). A first end of a flexible tube 64 is coupled to the proximal end of channel 60, and a second end of the tube is coupled to vacuum source 50 (FIG. 1).

In the configuration shown in FIG. 2B, a plurality of channels 60 are provided. This configuration is otherwise generally similar to the configuration described above with reference to FIG. 2A.

In the configuration shown in FIG. 2C, channel 60 is distributed completely circumferentially around tool 30. The wall of the tool comprises an inner wall 66 and an outer wall 68, which together define channel 60 therebetween. Alternatively, channel 60 is distributed partially circumferentially around tool 30 (configuration not shown). This configuration is otherwise generally similar to the configuration described above with reference to FIG. 2A.

Regardless of the particular configuration of the channel(s) 60, tool 30 typically is generally cylindrical, and has a length L1 of between 10 and 40 mm, such as between 15 and 35 mm, an outer diameter D1 of between 8 and 16 mm, such as between 10 and 14 mm, and an inner diameter of between 7 and 15 mm, such as between 9 and 13 mm. Typically, tool 30 has a cross-sectional area at distal end 40 of between 38 and 177 mm2, such as between 63 and 133 mm2. For some applications, tool 30 is shaped so as to define a proximal lip 69, which aids the surgeon in manipulating the tool (e.g., withdrawing the tool upon completion of the procedure). Typically, the tool comprises a metal, such as stainless steel.

Reference is made to FIG. 3, which is a schematic illustration of the insertion of an imaging probe 70 through outer tool 30, in accordance with an application of the present invention. After outer tool 30 has been held against pericardium 38, optionally using suction, as described hereinabove with reference to FIG. 1, the surgeon introduces a first penetration tool through a lumen 72 of tool 30, and uses the first penetration tool to puncture the pericardium to form a first passage 74 therethrough, which is typically generally circular, and large enough to accommodate passage therethrough of tool 90, described hereinbelow with reference to FIG. 4. The surgeon then withdraws the first penetration tool from the lumen of the outer tool. (This puncturing step is not shown in the figure.)

After forming first passage 74, the surgeon inserts imaging probe 70 through lumen 72 of outer tool 30 and first passage 74 into pericardial space 76. For some applications, imaging probe 70 comprises an optic fiber, an optical image sensor (e.g., a CCD or CMOS sensor), or an ultrasound transducer. The surgeon uses the imaging probe to locate a desired second site 78 on an outer surface 80 of a myocardium 82, typically at an upper region of an apex 84 of the heart, at a site that avoids the coronary arteries. This imaging step is optional, and for some applications it is not performed.

Reference is made to FIG. 4, which is a schematic illustration of the insertion of an inner tubular tool 90 through outer tool 30, in accordance with an application of the present invention. After second site 78 on outer surface 80 of myocardium 82 has been located, the surgeon introduces a second tubular tool 90 through lumen 72 of tool 30 and first passage 74, and advances tool 90 to second site 78. For some applications, the surgeon uses inner tool 90 to apply suction to outer surface 80 of myocardium 82 from a distal end 92 of the tool, in order to tightly hold the myocardium against distal end 92 of tool 90. In order to apply the suction, a vacuum source (either vacuum source 50 or a separate vacuum source) is coupled to one or more suction channels that pass through the tool and are open through respective inner-tool suction ports at the distal end thereof, via a flexible tube 94. These suction channels are typically similar to suction channels 60 of outer tool 30, and may be configured as described hereinabove with reference to FIGS. 2A-C. Alternatively, for other applications, suction is not applied.

Inner tool 90 typically has a length of between 20 and 50 mm, such as between 25 and 45 mm, an outer diameter of between 7 and 15 mm, such as between 9 and 13 mm, and an inner diameter of between 6 and 14 mm, such as between 8 and 12 mm. Typically, tool 90 has a cross-sectional area at distal end 92 of between 28 and 154 mm2, such as between 50 and 113 mm2.

Figure 5C:
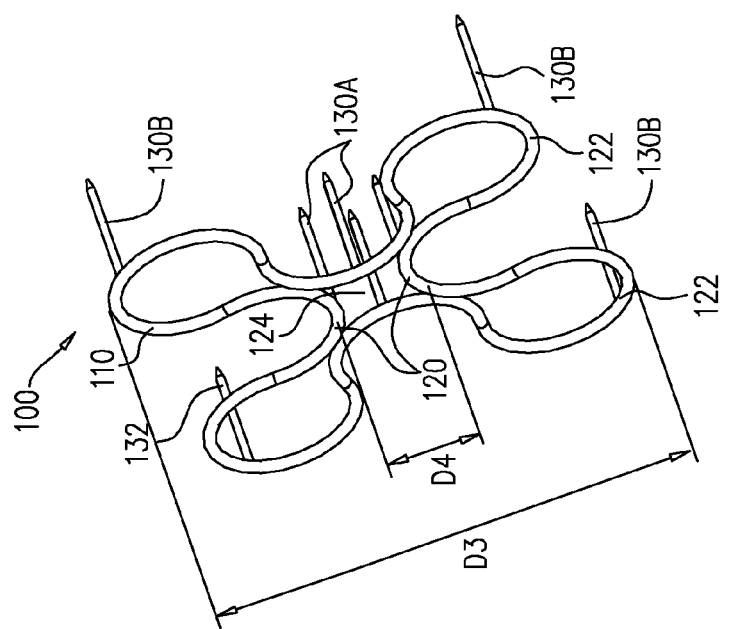
FIGS. 5C, 5D, and 5E are schematic illustrations of another configuration of the surgical closure device of FIGS. 5A and 5B in open, partially closed, and closed shapes, respectively, in accordance with an application of the present invention.
Figure 5D:
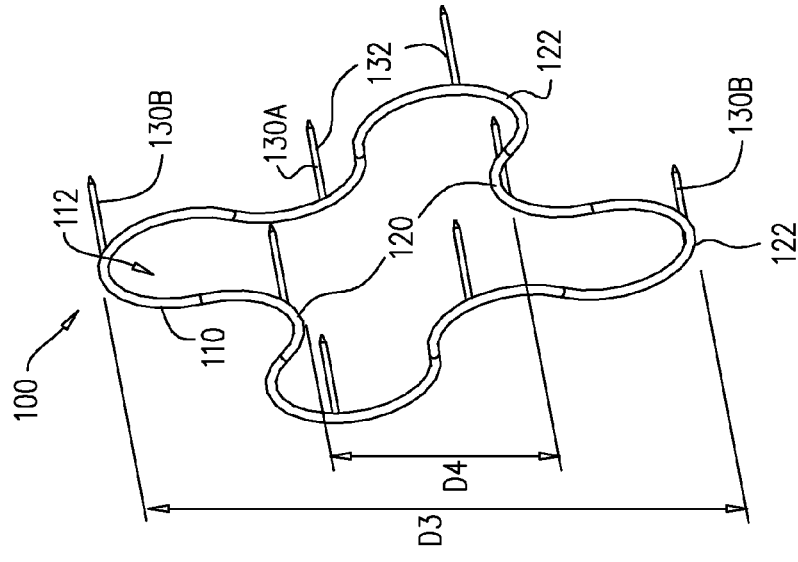
Figure 5E:
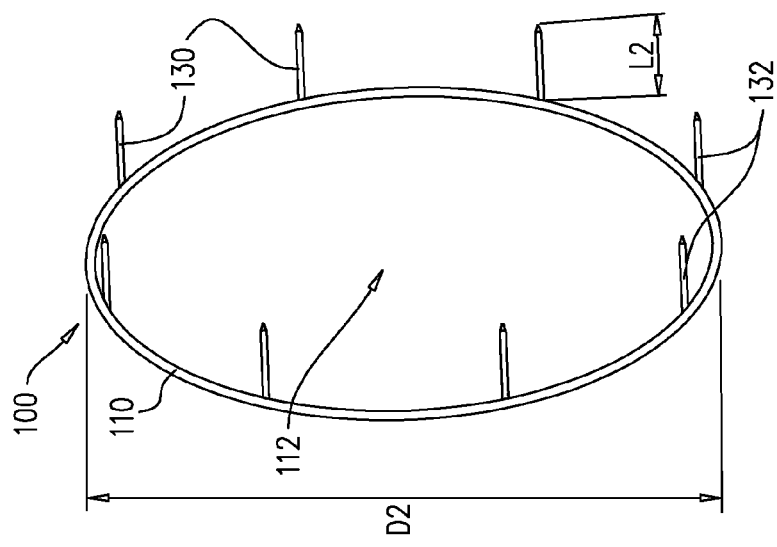

Reference is made to FIGS. 5A and 5B, which are schematic illustrations of a surgical closure device 100 in open and closed shapes, respectively, in accordance with an application of the present invention. Reference is also made to FIGS. 5C, 5D, and 5E, which are schematic illustrations of another configuration of surgical closure device 100 in open, partially closed, and closed shapes, respectively, in accordance with an application of the present invention. Closure device 100 comprises a continuous loop 110, which defines an opening 112 therethrough. For some applications, loop 110 is flat in the open, partially closed, and closed shapes, i.e., would define exactly one plane if the wire of the loop were to be conceptualized as a line without thickness; if placed on a flat surface, the loop would touch the surface at all point along the entire loop. Alternatively, the loop is generally, but not entirely, flat.

The loop is configured to assume at least:
an open shape, such as shown in FIGS. 5A and 5C, in which opening 112 has an open-shape area of between 28 and 314 mm2, such as between 50 and 255 mm2, e.g., about 314 mm2 For some applications, the open shape is a circle, as shown in FIGS. 5A and 5C, in which case the circle may have a diameter D2 of between 8 and 30 mm, such as between 10 and 25 mm, e.g., 20 mm. For other applications the shape is an ellipse, a square, another polygon (configuration not shown), or another shape, such as described hereinbelow with reference to FIG. 10A; and
a closed shape, such as shown in FIGS. 5B and 5E, in which opening 112 has a closed-shape area that is between 20% and 80% of the open-shape area (e.g., less than 80% of the open-shape area, such as less than 60% or less than 40% of the open-shape area). For example, the closed-shape area may be between 10 and 565 mm2, such as between 15 and 393 mm2. In the closed shape, loop 110 is shaped so as to define: (a) two or more inwardly-extending portions 120, which extend toward a central region 124 of loop 110, and (b) two or more outwardly-extending portions 122, which extend away from central region 124. Inwardly-extending portions 120 alternate with outwardly-extending portions 122 around loop 110. The closed shape thus may be similar to the shape of an asterisk or a flower. For some applications, in the closed shape, loop 110 is shaped so as to define between two and ten inwardly-extending portions 120 and between two and ten outwardly-extending portions 122, such as exactly two, exactly three, or exactly eight of each type of portion. For some applications, a greatest distance D3 across the closed shape is between 5 and 15 mm, e.g., 12 mm, and a closest distance D4 between any two inwardly-extending portions 120 is between 3 and 14 mm, e.g., 8 mm.

For some applications, as shown in FIG. 5D, loop 110 is configured to further assume a partially closed shape, in which opening 112 has a partially closed-shape area that is greater than the closed-shape area and less than the open-shape area, such as between 50% and 90% of the open-shape area, e.g., between 60% and 75% of the open-shape area. For example, the partially closed-shape area may be between 25 and 636 mm2, such as between 30 and 530 mm2. In the partially closed shape, loop 110 is typically shaped so as to define two or more inwardly-extending portions 120 that alternate with two or more outwardly-extending portions 122. When the loop assumes the partially closed shape, the inwardly-extending portions extend inwardly less than when the loop assumes the closed shape. The partially closed shape thus may be similar to the shape of an asterisk or a flower. For some applications, greatest distance D3 across the partially closed shape is between 12 and 22 mm, e.g., 15 mm, and closest distance D4 between any two inwardly-extending portions 120 is between 6 and 16 mm, e.g., 9 mm.

Closure device 100 further comprises four or more tissue anchors 130. Tissue anchors 130 are shaped so as to define respective anchoring portions 132, and, optionally, respective non-anchoring alignment portions 134, as described hereinbelow with reference to FIGS. 10A-B and 11A-B. Anchoring portions 132 are typically straight. The anchors are coupled to loop 110 such that when the loop assumes the open shape, each of anchoring portions 132 defines an angle of between 75 and 115 degrees with a plane defined by the opening, such as between 85 and 95 degrees, e.g., 90 degrees. Typically, closure device comprises between 6 and 20 anchors 130, such as exactly 8 or exactly 12 anchors. For some applications, the number of anchors equals the sum of the number of inwardly-extending portions 120 and the number of outwardly-extending portions 122. Alternatively, the number of anchors is less than or greater than the sum. Typically, each of anchors 130 has a length L2 of between 2 and 10 mm, such as between 5 and 6 mm (e.g., 8 mm), or between 1 and 6 mm, such as between 2 and 5 mm (e.g., 3 mm).

For some applications, at least a portion (such as all) of the tissue anchors are shaped to define respective barbs at their distal ends. The barbs help couple the anchors to the muscle tissue of the myocardium, generally irreversibly. Alternatively, some or all of the anchors are not shaped so as to define barbs. The lack of barbs allows the tissue anchors (and the closure device) to be removed from the muscle tissue if necessary, such as in order to reposition the closure device if clinically necessary.

For some applications, when loop 110 assumes the closed shape, such as shown in FIGS. 5B and 5E, a first set of two or more of tissue anchors 130 (labeled 130A in FIGS. 5B and 5E) are coupled to respective inwardly-extending portions 120, and a second set of two or more of the tissue anchors (labeled 130B in FIGS. 5B and 5E) are coupled to respective outwardly-extending portions 122. For some applications, each of anchors 130A of the first set is coupled to the most inwardly-extending location on its respective inwardly-extending portion 120, or in a vicinity of this location, e.g., within 1 mm thereof, such as within 0.5 mm thereof. Alternatively, some or all of anchors 130A of the first set are coupled to inwardly-extending portions 120 elsewhere along the portions. Similarly, for some applications, each of anchors 130B of the second set is coupled to the most outwardly-extending location on its respective outwardly-extending portion 122, or in a vicinity of this location, e.g., within 1 mm thereof, such as within 0.5 mm thereof. Alternatively, some or all of anchors 130B of the second set are coupled to outwardly-extending portions 122 elsewhere along the portions.

Figure 6:
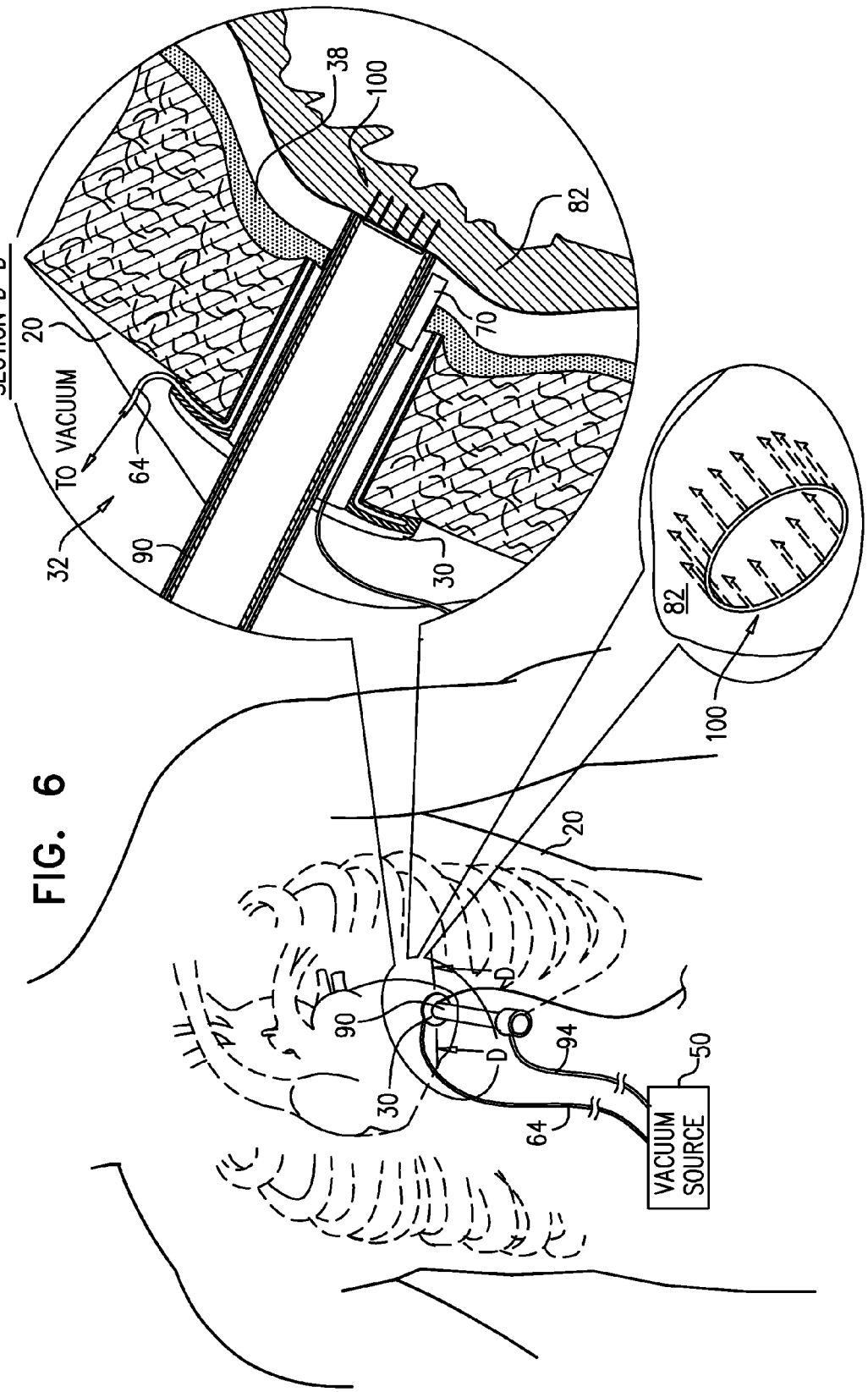
FIG. 6 is a schematic illustration of the attachment of the closure device of FIGS. 5A and 5B to a myocardium, in accordance with an application of the present invention.

Reference is made to FIG. 6, which is a schematic illustration of the attachment of closure device 100 to myocardium 82, in accordance with an application of the present invention. While inner tool 90 is held against myocardium 82, optionally using suction, as described hereinabove with reference to FIG. 4, the surgeon introduces closure device 100 through inner tool 90, while the closure device assumes its open shape. The surgeon attaches the closure device to the myocardium, by inserting the anchors into the cardiac tissue.

Figure 7A:
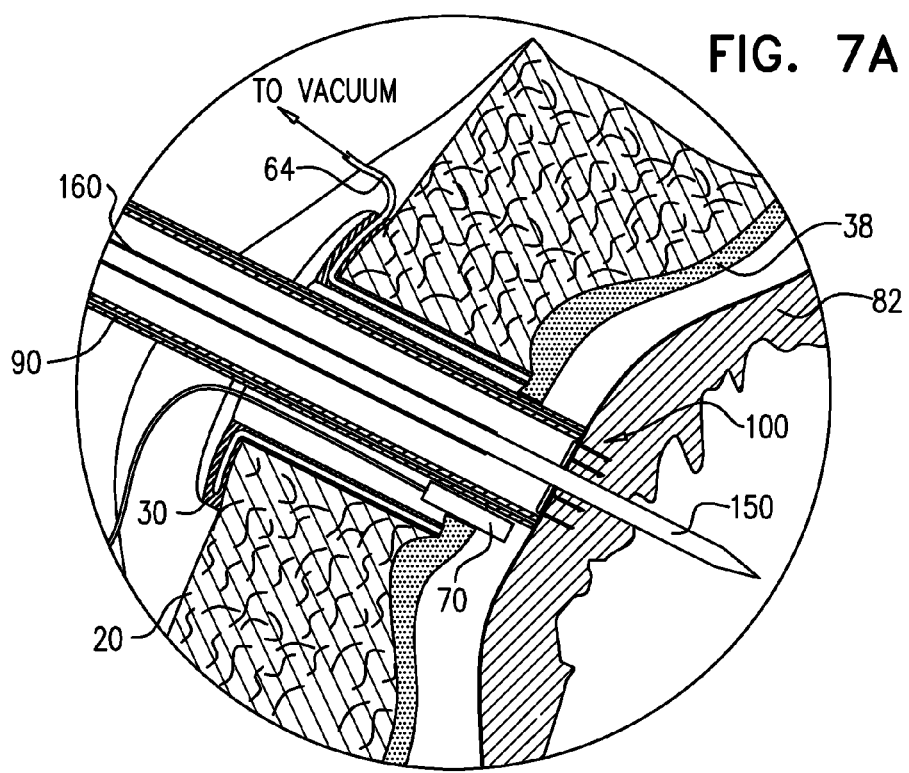
FIGS. 7A and 7B are schematic illustrations of the performance of a Seldinger technique through the myocardium and the open closure device of FIGS. 5A and 5B, in accordance with an application of the present invention.
Figure 7B:
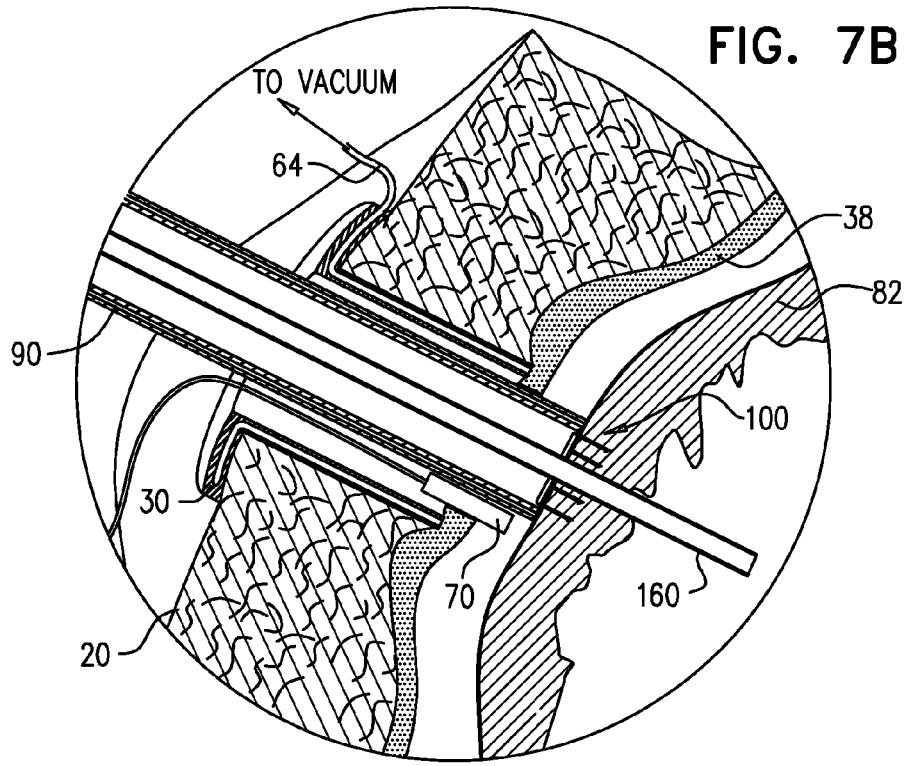

FIGS. 7A and 7B are schematic illustrations of the performance of a Seldinger technique through myocardium 82 and open closure device 100, in accordance with an application of the present invention. While the closure device remains in its open shape attached to the myocardium, the surgeon passes a needle 150 through inner tubular tool 90 and the open closure device, and punctures the myocardium to form a second passage therethrough, as shown in FIG. 7A. The surgeon advances a guidewire through the needle, withdraws the needle leaving the guidewire in the heart, passes a catheter 160 over the guidewire, and withdraws the guidewire (in order to focus the figures on the novel aspects of the invention, these well-known steps of the Seldinger technique are not shown). Guidewire 160 remains in the heart, as shown in FIG. 7B.

Alternatively, the surgeon does not use the Seldinger technique, and instead introduces another second penetration tool through inner tubular tool 90, and uses the second penetration tool to puncture the myocardium to form the second passage therethrough.

Figure 8A:
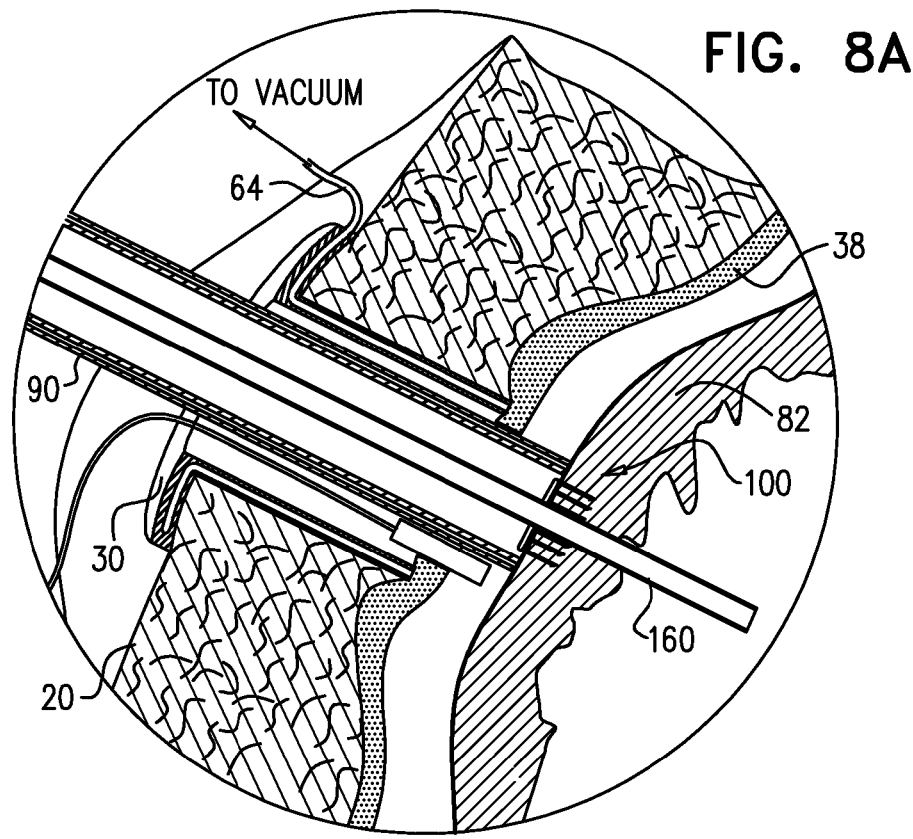
FIGS. 8A and 8B are schematic illustrations of the closure device of FIGS. 5A and 5B having a partially closed shape, in accordance with an application of the present invention.
Figure 8B:
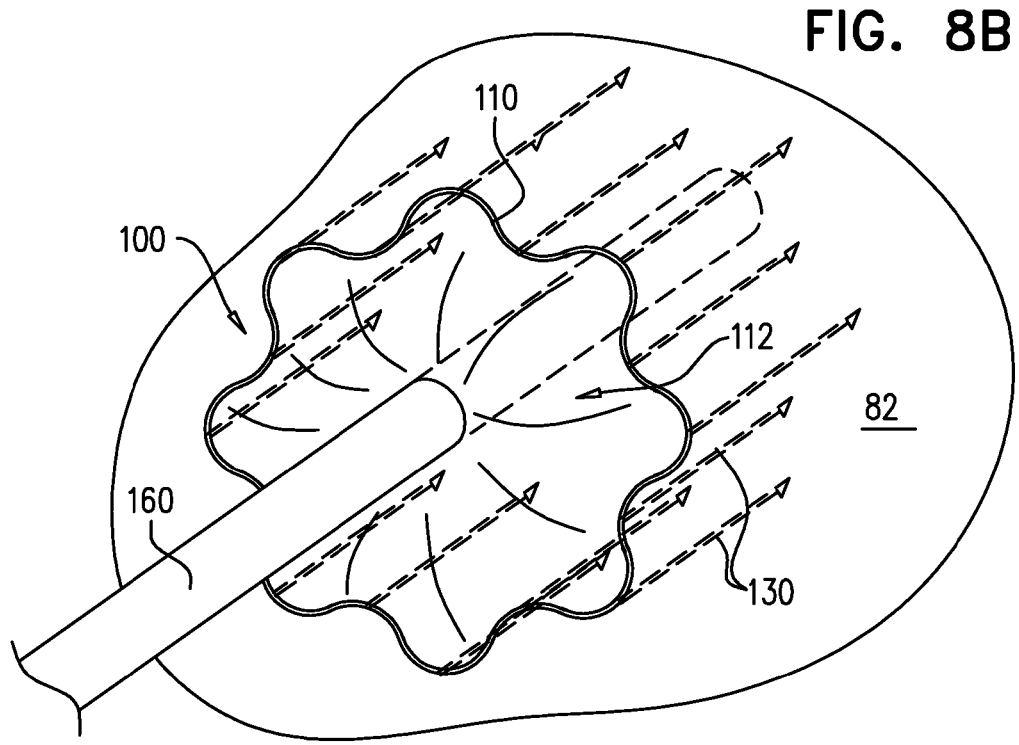

FIGS. 8A and 8B are schematic illustrations of closure device 100 having a partially closed shape, in accordance with an application of the present invention. Optionally, after passing catheter 160 through closure device 100 and into the heart, as described hereinabove with reference to FIGS. 7A and 7B, the surgeon causes closure device 100 to assume a partially closed shape, in which opening 112 has a partially closed-shape area that is greater than the closed-shape area and less than the open-shape area, such as described, for example, hereinabove with reference to FIG. 5D. This partial contraction of loop 110 causes anchors 130 to move inwardly and to squeeze together the cardiac tissue of myocardium 82 around catheter 160, thereby preventing or reducing bleeding during the procedure. In order to cause the closure device to assume the partially closed shape, the surgeon may regulate the temperature of the device (cool or heat), apply a current thereto, and/or modulate a current already applied thereto.

The surgeon performs a medical procedure on the heart through catheter 160 (i.e., via the second passage through the myocardium described above). For example, medical procedures that may be performed through the catheter when inserted into the left ventricle include, but are not limited to:
  valve replacement, such as aortic or mitral valve replacement;
  valve repair, such as aortic or mitral valve repair;
  left atrium ablation;
  ascending, arch, and descending aortic stenting; and
  left ventricle cardiac resynchronization therapy.

Medical procedures that may be performed through the catheter when inserted into the right ventricle include, but are not limited to:
  valve repair, such as tricuspid valve repair;
  right heart ablation; and
  pulmonary artery embolectomy.

Figure 9A:
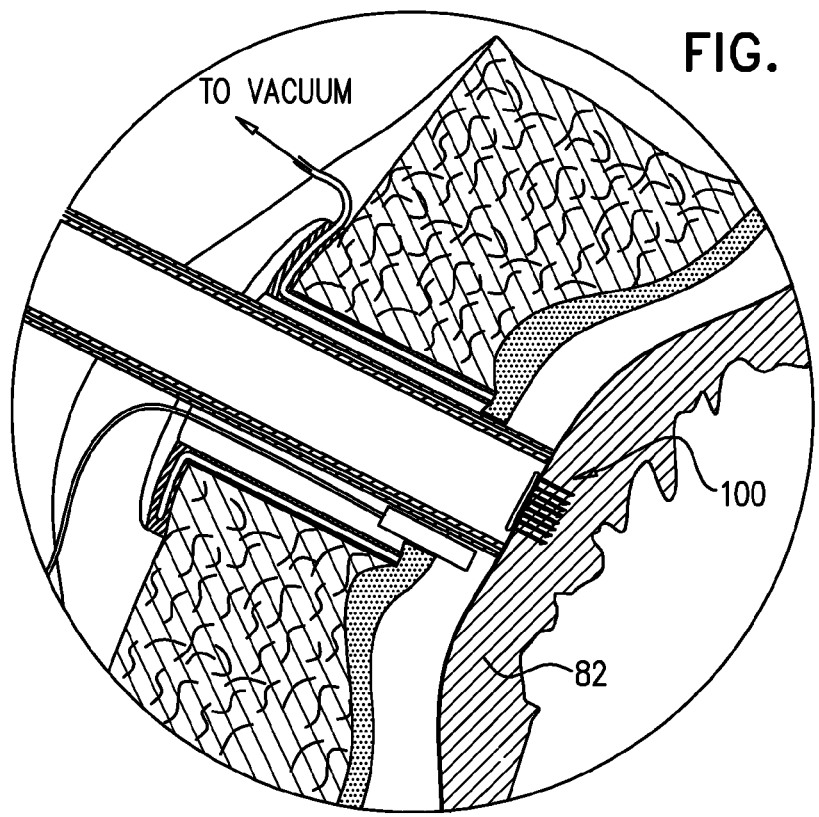
FIGS. 9A and 9B are schematic illustrations of the closure device of FIGS. 5A and 5B in its closed shape, in accordance with an application of the present invention.
Figure 9B:
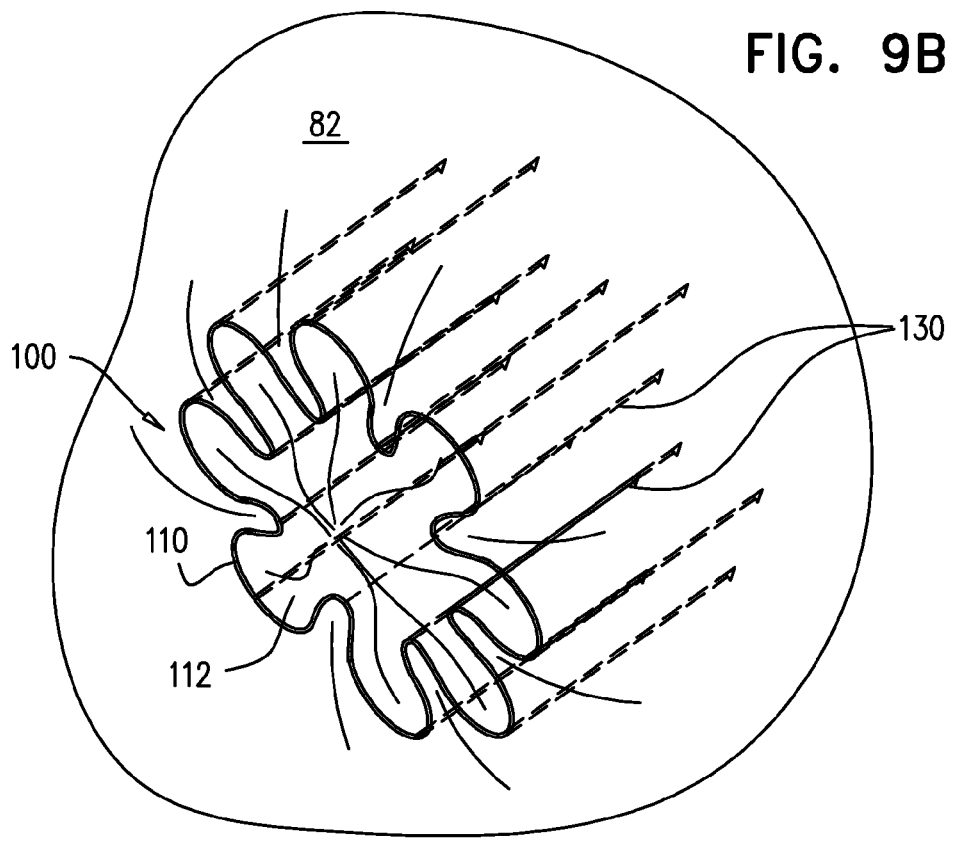

Reference is made to FIGS. 9A and 9B, which are schematic illustrations of closure device 100 in its closed shape, in accordance with an application of the present invention. After performing the medical procedure, the surgeon removes catheter 160 from the heart, and allows or causes closure device 100 to assume the closed shape, as described hereinabove with reference to FIG. 5B. For example, the surgeon may cause the closure device to assume the closed shape by actively changing (increasing or decreasing) the temperature of the loop, or passively allowing the temperature of the loop to approach the body's internal temperature, such as by ceasing to actively maintain a different temperature, and/or ceasing to apply an electric current to the loop. As shown in FIG. 9B, the contraction of loop 110 causes anchors 130 to move inwardly and squeeze together the cardiac tissue of myocardium 82 surrounding the passage made through the myocardium.

Figure 10A:
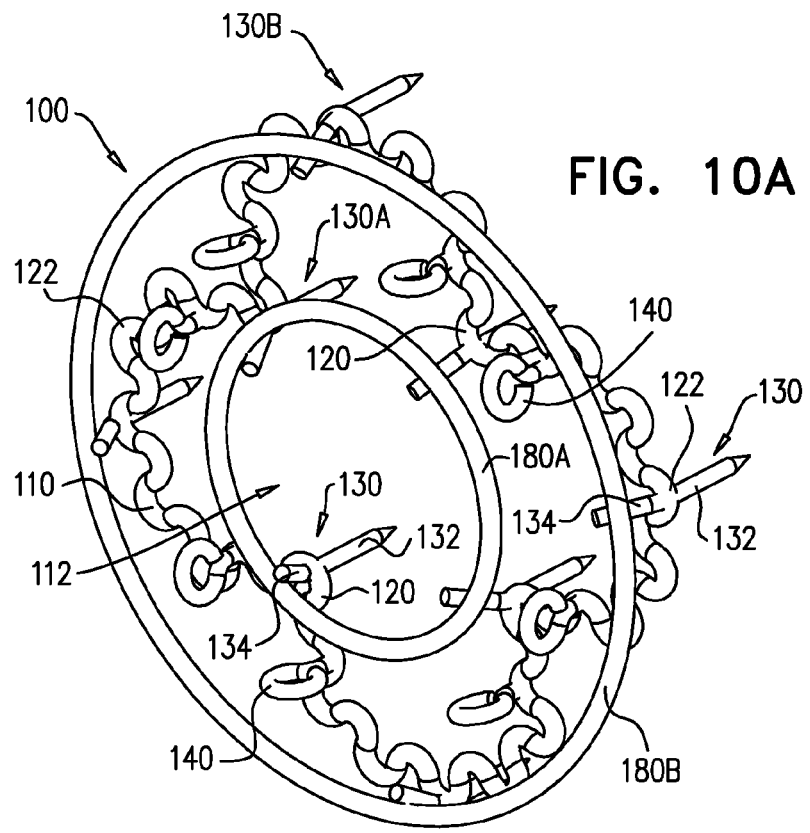
FIGS. 10A and 10B are schematic illustrations of another configuration the surgical closure device of FIGS. 5A-E in open and closed shapes, respectively, in accordance with an application of the present invention.
Figure 10B:
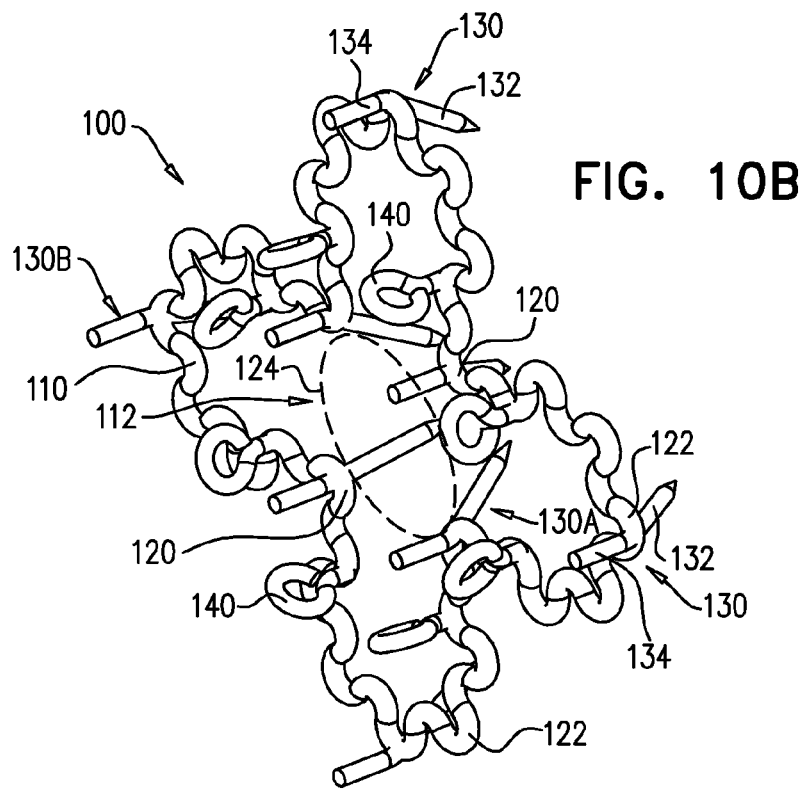

Reference is now made to FIGS. 10A and 10B, which are schematic illustrations of another configuration of surgical closure device 100 in open and closed shapes, respectively, in accordance with an application of the present invention. Except as described below, this configuration is generally similar to the configuration of closure device 100 described hereinabove with reference to FIGS. 5C-E. In this configuration, even when loop 110 assumes the open shape, the loop is shaped so as to define two or more inwardly-extending portions 120 that alternate with two or more outwardly-extending portions 122. When the loop assumes the open shape, the inwardly-extending portions extend inwardly less than when the loop assumes the closed shape. The inwardly- and outwardly-extending portions predispose the loop to bend at desired locations when transitioning from the open to the closed shapes, so that the loop assumes the desired closed shape. As in the configurations described hereinabove with reference to FIGS. 5A-E, in the configuration of FIGS. 10A-B loop 110 is typically flat in the open and closed shapes.

For some applications, closure device 100 is configured to assume the closed shape when unconstrained. The closure device is initially constrained in the open shape by a tool, as described hereinbelow. Upon removal of the tool, the closure device automatically assumes the closed shape. For these applications, closure device 100 typically comprises an elastic metal, such as elastic stainless steel.

For other application, closure device 100 comprises a non-elastic metal, such as a malleable metal, and a tool is provided that is configured to apply a force to the loop that transitions the closure device from the open shape to the closed shape, such as by squeezing on the loop at appropriate locations therearound. The tool may apply the force directly to the loop, to extension members 140, and/or to non-anchoring alignment portions 134. In these applications, the surgeon can decide how tightly to close the loop, as appropriate for a particular procedure and patient.

For some applications, the inwardly-extending and outwardly-extending portions of loop 110 are wavy, both when the loop assumes the open shape and when the loop assumes the closed shape. For example, both portions may define small sine waves. Typically, the waves are oriented such that the loop remains flat, i.e., the waves are within the plane defined by the loop. The waviness provides added length to the loop, which provides the loop with the flexibility necessary for enabling the loop to transition from the open shape to the closed shape, even when the loop comprises a relatively inflexible material, such as stainless steel (which is relatively inflexible compared to Nitinol, which the loop may comprise in the non-wavy configurations shown in FIGS. 5A-E).

For some applications, tissue anchors 130 are shaped so as to define respective anchoring portions 132 and respective non-anchoring alignment portions 134. Anchoring portions extend from loop 110 in a first direction into a first space on a first side of the plane defined by opening 112 (toward the cardiac tissue). Non-anchoring alignment portions 134 extend from loop 110 in a second direction into a second space on a second side of the plane defined by the opening (away from the cardiac tissue). Each of tissue anchors 130 typically comprises a single metal element that passes through and is coupled to loop 110. The metal element is sufficiently rigid such that changing the angles of the non-anchoring alignment portions with the plane causes associated changes of the angles of the respective anchoring portions with the plane. For some applications, the non-anchoring portion and anchoring portion of a tissue anchor define an angle therebetween of between 135 and 165 degrees, such as 150 degrees.

For some applications, anchoring portions 132 are configured to assume respective initial angular orientations, such as when anchors 130 are constrained, in which the anchors are configured such that:

each of anchoring portions 132 defines an angle of between 75 and 115 degrees, e.g., between 85 and 95 degrees, such as 90 degrees, with the plane defined by opening 112; and/or each of non-anchoring alignment portions 134 defines an angle of between 45 and 75 degrees, e.g., between 55 and 65 degrees, such as 60 degrees, with the plane defined by opening 112.

For some applications, anchors 130 are configured to assume respective tissue-locking angular orientations, such as when anchors 130 assume respective unconstrained states, in which the anchors are configured such that:

each of anchoring portions 132 defines an angle of between 45 and 75 degrees, e.g., between 55 and 65 degrees, such as 60 degrees, with the plane defined by opening 112. Anchoring portions 132 typically are oriented toward an axis of closure device 100 that is perpendicular to the plane defined by opening 112 and passes through central region 124; and/or each of non-anchoring alignment portions 134 defines an angle of between 75 and 115 degrees, such as 90 degrees, with the plane defined by opening 112.

It is noted that the angular orientations of the anchors are independent of the open/closed shape of loop 110. The anchoring portions may be transitioned from their initial angular orientations to their tissue-locking angular orientations either before or after the loop is transitioned from its open shape to its closed shape. For some applications, the closure device and/or a tool used to implant the device are configured to prevent the surgeon from leaving the anchors unlocked when the loop is in the closed shape.

When anchoring portions 132 assume the tissue-locking angular orientations, the angles of anchoring portions 132 help couple the anchors to the cardiac tissue, and thus serve to lock the anchors to the cardiac tissue. In addition, when loop 110 assumes the closed shape, as shown in FIG. 10B, or a partially closed shape, the angling of the anchoring portions increases the inwardly-directed pressure applied by closure device 100 to the cardiac tissue, thereby helping close the puncture through the heart wall. For applications in which the anchors are locked before the loop is transitioned to the closed shape, the locking may help secure the loop to the cardiac tissue during a procedure performed through the loop and/or during the transition to the closed shape.

For some applications, anchors 130 are constrained in the initial angular orientations at least during attachment of closure device 100 to the myocardium, as shown in FIG. 10A, typically when the closure device is in the open shape. For some applications, one or more constraining members, such as rings 180, may be provided to hold the anchors in the initial angular orientations. For example, the rings may comprise a first inner ring 180A and a second outer ring 180B. The rings are configured and sized to deflect non-anchoring portions 134 of anchors 130 away from their unconstrained angles with respect to the plane defined by opening 112. Such deflection causes anchoring portions 132 to become more perpendicular with the plane. For example, the rings may cause each of the non-anchoring portions to define an angle of between 45 and 75 degrees with the plane, such as 60 degrees, thereby causing the anchoring portions to define an angle of 75 and 115 degrees with the plane, such as 90 degrees. This angle facilitates penetration of the anchoring portions into the cardiac tissue.

The constraining members (e.g., rings 180) are typically put in place during manufacture of closure device 100, and removed during the surgical procedure after the closure device has been attached to the myocardium. For example, the constraining members may be removed using a tool such as pliers. Typically, the rings are elliptical, such as circular. For some applications, inner ring 180A has an inner diameter of between 8 and 18 mm, and outer ring 180B has an inner diameter of between 15 and 30 mm.

Alternatively, for some applications, the constraining members are integrated into a surgical tool, such as tool 190 described hereinbelow with reference to FIG. 12A-B. For these applications, the constraining members may comprise anchor-specific arms that prevent the anchors from assuming their unconstrained states. The arms may then be folded back onto the tool in order to enter and exit the patient's body (typically using a narrower passage than that required for the rings).

For some applications, the constraining members, or an additional set of constraining members, are used to cause the anchors to reassume the initial constrained states after the anchors have been coupled to the cardiac tissue. This facilitates decoupling of the closure device from the cardiac tissue if necessary.

Reference is still made to FIGS. 10A-B. For some applications, closure device 100 further comprises a plurality of extension members 140, which are coupled to loop 110, and which extend from the loop in a direction generally opposite anchoring portions 132. (For example, the anchoring portions may extend from the loop in a first direction into a first space on a first side of the plane defined by opening 112 (toward the cardiac tissue), and the extension members may extend from the loop in a second direction into a second space on a second side of the plane (away from the cardiac tissue).) The extension members may be shaped, for example, so to define shapes selected from the group consisting of: rings (as shown), hooks, tabs, and rods (configurations not shown). Typically, the extension members define an angle of between 75 and 105 degrees, e.g., 90 degrees, with the plane defined by opening 112. The extension members generally serve one or both of the following purposes:

the extension members provide surfaces against which one or more surfaces of a surgical tool, such as tool 190 described hereinbelow with reference to FIG. 12A-B, apply a radially outwardly directed force, thereby holding loop 110 in the open shape; and/or the extension members serve as engagement members, which are engaged by engagement elements of a surgical tool, such as protrusions 192 of tool 190, described hereinbelow with reference to FIGS. 12A-B. When thus engaged, closure device 100, when at least partially coupled to the cardiac tissue, serves to hold the tool in place near or against the cardiac tissue.

For applications in which the extension members are shaped so as to define rings, the rings may have an inner diameter of between 0.5 and 2 mm, such as 1 mm.

Figure 11A:
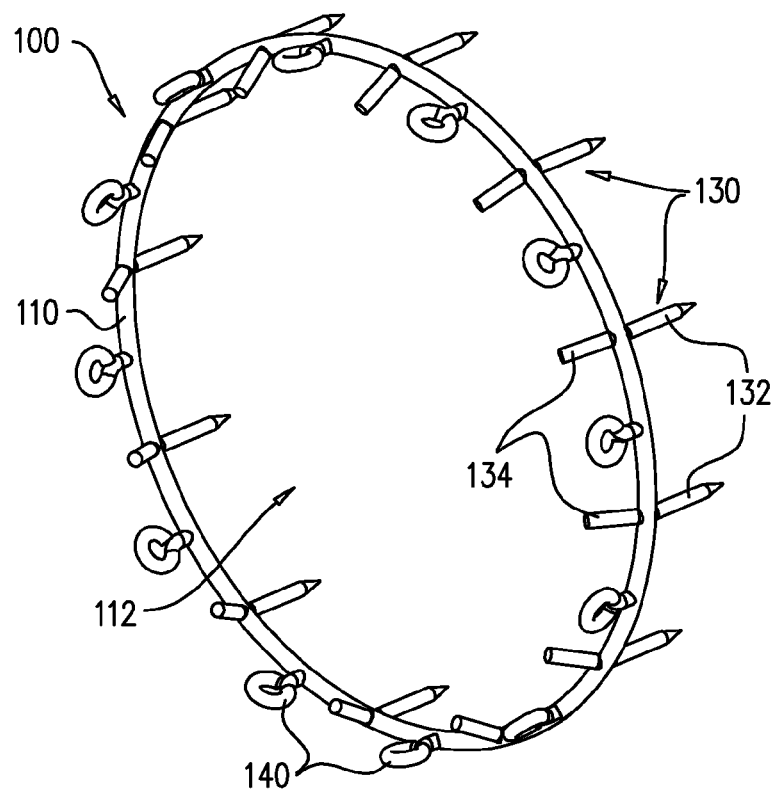
FIGS. 11A and 11B are schematic illustrations of yet another configuration of the surgical closure device of FIGS. 5A-E in open and closed shapes, respectively, in accordance with an application of the present invention.
Figure 11B:
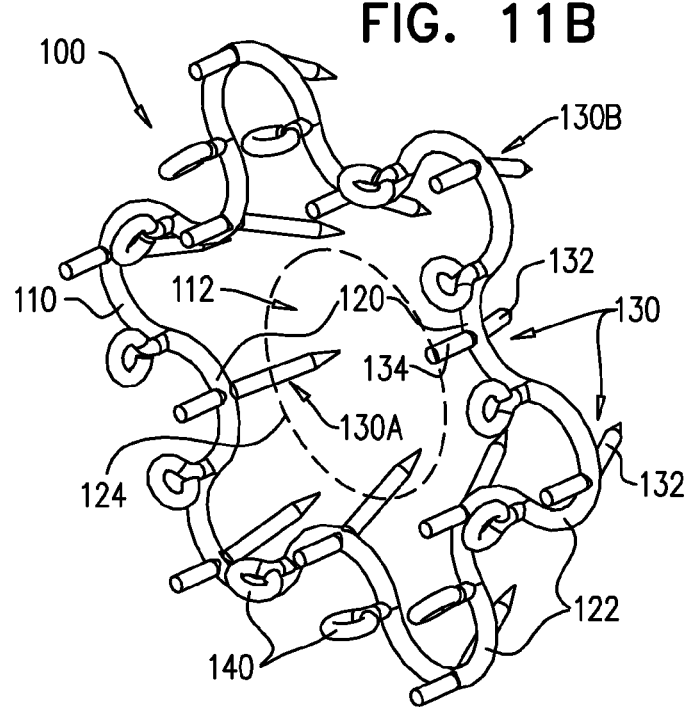

Reference is now made to FIGS. 11A and 11B, which are schematic illustrations of yet another configuration of surgical closure device 100 in open and closed shapes, respectively, in accordance with an application of the present invention. Except as described below, this configuration is generally similar to the configuration of closure device 100 described hereinabove with reference to FIGS. 5C-E. In this configuration, tissue anchors 130 are shaped so as to define respective anchoring portions 132, and respective non-anchoring alignment portions 134, such as described hereinabove with reference to FIGS. 10A-B. Optionally, closure device 100 further comprises extension members 140, such as described hereinabove with reference to FIGS. 10A-B. For some applications, at least one constraining member, such as at least one of rings 180, described hereinabove with reference to FIG. 10A, is provided to hold the anchors in the initial constrained states (configuration not shown in FIG. 11A). For some applications, anchors 130 are configured to transition their angular orientations from the orientations shown in FIG. 11A to the orientations shown in FIG. 11B to lock the anchoring portions to the cardiac tissue, as described hereinabove with reference to FIGS. 10A-B. As in the configurations described hereinabove with reference to FIGS. 5A-E and 10A-B, in the configuration of FIGS. 11A-B loop 110 is typically flat in the open and closed shapes.

Reference is again made to FIGS. 5A-E, 10A-B, and 11A-B. Typically, loop 110 is configured such that, as the loop transitions from the open shape to the closed shape, all of anchors 130 move in generally radial directions (inwardly towards central region 124), and do not move in generally circumferential directions. Such radial motion is less likely to tear or otherwise damage the tissue of the myocardium than is circumferential motion.

For some applications, loop 110 is configured such that, as the loop transitions from the open shape to the closed shape, anchors 130A of the first set move on average a first distance and anchors 130B of the second set move on average a second distance that is less than the first distance. Movement by these two distances has the effect of applying two strengths of closure on the heart muscle: an inner, greater level of closure, surrounded by an outer, lesser level of closure. Together, the two levels of closure together tightly close the passage made through the myocardium, while minimizing the risk of damaging heart tissue. For example the first distance may be between 2 and 10 mm, e.g., between 4 and 10 mm, or between 2 and 8 mm, such as 4 and 6 mm, e.g., 5 mm, and the second distance may be between 2 and 4 mm, such as 3 mm, or between 40% and 80% of the first distance, such as between 50% and 70%, e.g., 60%.

For some applications, the anchors of both the first and second sets are coupled to respective inwardly-extending portions 120. For example, in order to cause the movement of the first and second distances mentioned above, when the loop assumes the closed shape, the inwardly-extending portions to which the anchors of the first set are coupled extend inwardly a greater distance than do the inwardly-extending portions to which the anchors of the second set are coupled.

Reference is again made to FIGS. 5A-E, 10A-B, and 11A-B. For some applications, loop 110 comprises a shape memory alloy, such as nickel-titanium (NiTi) (Nitinol), copper-zinc-aluminum-nickel, or copper-aluminum-nickel. A shape memory alloy may be particularly appropriate for the configurations of loop 110 described hereinabove with reference to FIGS. 5A-E and/or 11A-B; a shape memory alloy may also be appropriate for the configuration of loop 110 described hereinabove with reference to FIGS. 10A-B. In these applications, loop 110 transitions between the open and closed shapes responsively to a change in temperature of the loop. Typically, the shape memory alloy of the loop has been trained to assume the closed shape at least within a normal internal body temperature, e.g., within a temperature range of 36 to 40° C. Typically, the alloy is configured to assume the open position by reducing the temperature of the loop to below this temperature range. For example, the loop may be cooled and kept cool until immediately before use. Alternatively, the alloy is configured to assume the open position by driving a current through the loop, thereby activating the alloy to change shape using a mechanism not mediated by temperature change. Further alternatively, the alloy is activated to change shape using another activation technique known in the shape memory art.

For some applications, the shape memory alloy exhibits one-way memory. The alloy is trained to assume the closed shape within a certain temperature range that includes normal internal body temperature. Prior the procedure, either at the time of manufacture or immediately prior to performance of the heart procedure, the loop is manipulated into the open shape while at a temperature outside of the memory temperature range (typically a temperature below the memory temperature range). When the temperature of the loop enters the memory temperature range in the body of the subject, the loop assumes the remembered shape.

For other applications, the shape memory allow exhibits two-way memory. The alloy is trained to assume the closed shape within a first temperature range that includes normal internal body temperature (e.g., within a temperature range of 36 to 40° C.), and to assume the open shape with a second temperature range outside normal internal body temperature. Immediately prior to and during the first steps of the procedure, the loop is held at a temperature within the second temperature range, and thus assumes the remembered open shape. When the loop is no longer held at this temperature, and thus enters the first temperature range in the body of the subject, the loop assumes the remembered closed shape.

Reference is again made to FIGS. 5A-E, 10A-B, and 11A-B. For some applications, loop 110 comprises a superelastic metal, or an elastic metal, such as elastic stainless steel. An elastic metal may be particularly appropriate for the configurations of loop 110 described hereinabove with reference to FIGS. 10A-B; an elastic metal may also be appropriate for the configurations of loop 110 described hereinabove with reference to 5A-E and/or 11A-B. In these applications, loop 110 typically transitions between the open and closed shapes upon removal a tool preventing the transition.

Reference is now made to FIGS. 12A-D, which are schematic illustrations of another surgical tool and another transapical surgical procedure, in accordance with an application of the present invention. The transapical surgical procedure is typically performed to form a passage through the left or right ventricle of a beating heart, near the apex of the ventricle. A catheter is inserted through the passage into the ventricle, and is used to access the heart for performing a medical procedure, such as valve replacement (e.g., aortic and mitral valve replacement), or valve repair (e.g., mitral valve repair). Although this procedure is illustrated with the configuration of surgical closure device 100 described with reference to FIGS. 10A-B, the procedure may also be performed using the configurations of surgical closure device 100 described hereinabove with reference to FIG. 5A-E or 11A-B.

As described hereinabove with reference to FIG. 1, a surgeon begins the procedure by making a small incision in the chest wall between two ribs, e.g., between the fourth and fifth ribs, or between the fifth and sixth ribs, depending on the location of the apex in the particular patient, typically after administering local anesthesia. The surgeon passes an outer tubular tool through the chest wall. The surgeon may use outer tubular tool 30 of transapical surgical system 32, described hereinabove with reference to FIGS. 1-4, 6, 7A-B, 8A, and 9A, or a conventional trocar. Typically, the ribs do not need to be spread, because of the small diameter of the tool. The surgeon introduces a first penetration tool through a lumen of the tool, and uses the first penetration tool to puncture the pericardium to form passage 74 therethrough (as described hereinabove with reference to FIG. 3), which is typically generally circular, and large enough to accommodate passage therethrough of tool 190, described hereinbelow with reference to FIGS. 12A-B. The surgeon then withdraws the first penetration tool from the lumen of the outer tool. (This puncturing step is not shown in the figure.) Optionally, imaging is performed, such as described hereinabove with reference to FIG. 3.

Figure 12A:
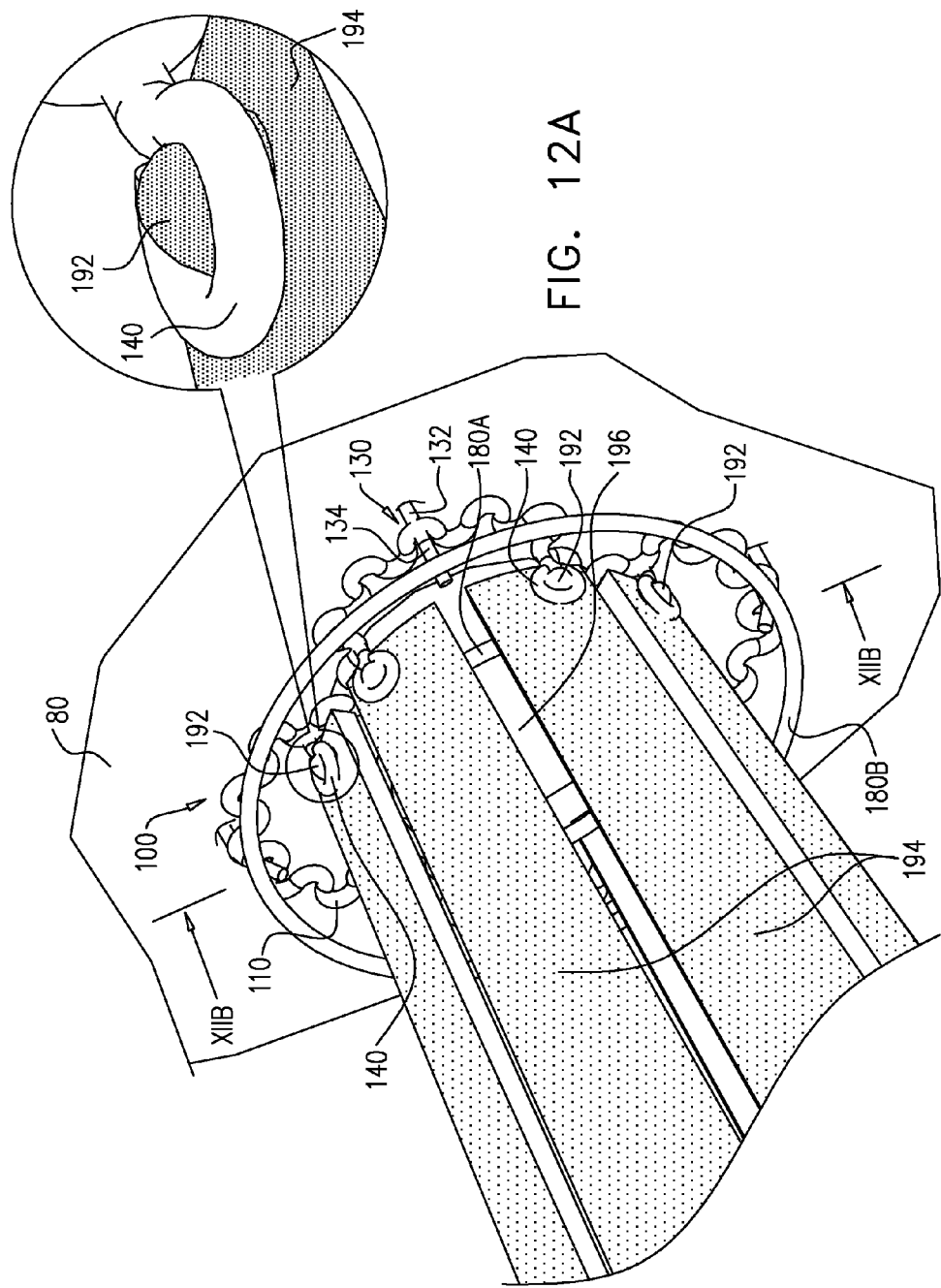

As shown in FIGS. 12A-B, the surgeon introduces a generally tubular tool 190, and advances tool 190 to site 78 on outer surface 80 of myocardium 82. Tubular tool 190 is introduced through a lumen of the outer tubular tool; the outer tubular tool is not shown in FIGS. 12A-B, but can be seen in FIG. 4. Before tool 190 is introduced, surgical closure device 100 is removably coupled to tool 190, such as during manufacturing of the tool and closure device, or by a healthcare worker prior to the procedure. The surgeon uses tool 190 to attach closure device 100 to the myocardium, by inserting the anchors into the cardiac tissue while loop 110 assumes its open shape. For some applications, tool 190 is configured to apply suction to outer surface 80 of myocardium 82 from a distal end of the tool, in order to assist holding the myocardium against the distal end of the tool, such as using the techniques described for tool 90 hereinabove with reference to FIG. 4. Alternatively, suction is not applied.

As described hereinabove with reference to FIG. 10A, for some applications one or more constraining members, such as rings 180, are provided to hold anchors 130 in their initial constrained states. By way of example, FIGS. 12A-B show first inner ring 180A and second outer ring 180B.

For some applications, tool 190 is shaped so as to define a plurality of engagement elements, such as protrusions 192, which are configured and positioned to initially engage respective engagement members 140 of closure device 100, as described hereinabove with reference to FIGS. 10A-B. The closure device, when at least partially coupled to the cardiac tissue, as shown in FIGS. 12A-B, holds tool 190 in place near or against the cardiac tissue. For some applications, the constraining members (e.g., rings 180) are removed while tool 190 is still coupled to the closure device. Removal of the constraining members allows anchoring portions 132 to transition to their tissue-locking angular orientations, as described hereinabove with reference to FIGS. 10B and 11B. This locking of the anchors to the cardiac tissue helps hold tool 190 in place near or against the cardiac tissue, in a manner similar to the suction ports of tool 90, as described hereinabove with reference to FIG. 4.

In some configurations, as shown in FIGS. 12A-B, protrusions 192 are disposed on an outer surface of tool 190. In these configurations, tool 190 may be configured to apply a radially outwardly directed force against the engagement members, thereby holding loop 110 of closure device 100 in the open shape. For some applications, tool 190 is shaped so as to define a plurality of elongated, generally flat members 194, which apply the force against the engagement members. Members 194 are distributed around the circumference of tool 130. Tool 190 is shaped so as to provide longitudinally-extending spaces 196 between the members when the members apply the force against the engagement members, as shown in FIGS. 12A-B. When members 194 are contracted in radially-inward direction (not shown), the members no longer apply the force, thereby allowing loop 110 to assume the closed shape. For some applications, external surfaces of members 194 are shaped so as to define protrusions 192. When members 194 are contracted, the protrusions disengage from extension members 140 of closure device 100.

For some applications, as shown in FIG. 12C, a Seldinger technique is performed through myocardium 82 and closure device 100, in accordance with an application of the present invention. While the closure device remains in its open shape or a partially closed shape attached to the myocardium, the surgeon passes needle 150 through tool 190 and the open closure device, and punctures the myocardium to form a passage therethrough. The surgeon advances a guidewire through the needle, withdraws the needle leaving the guidewire in the heart, passes a catheter over the guidewire, and withdraws the guidewire (in order to focus the figures on the novel aspects of the invention, these well-known steps of the Seldinger technique are not shown). The guidewire remains in the heart.

Alternatively, the surgeon does not use the Seldinger technique, and instead introduces another second penetration tool through tool 190, and uses the second penetration tool to puncture the myocardium to form the passage therethrough.

FIG. 12D shows closure device 100 in its closed shape coupled to myocardium 82, after tool 190 has been withdrawn, and rings 180 have been removed.

Reference is again made to FIGS. 5B, 5E, 9A-B, 10B, 11B, and 12D. If it should be necessary to perform an additional transapical procedure on the subject at a later time, closure device 100 is reopened by causing it to again assume its open shape. The closure applied by the device is thus conveniently reversible, and allows the subsequent passage of medical tools through the myocardium. In addition, because the closure device is easily visible using fluoroscopy, the closure device can be used in future follow-on procedures as a marker for an apical access point. The closure device may be reopened using a tool (e.g., similar to tool 190), such by attaching the tool to the closure device and using the tool to transition the loop back to its open shape. Alternatively or additionally, for applications in which the closure device comprises a shape memory alloy, the loop may be reopened by modifying the temperature of the device and/or applying a current to the device.

For some applications, tool 30, tool 90, and/or tool 190, when coupled to the heart, are used to align the insertion of needle 150 through the apex towards a designated site in the heart, such as an aortic or mitral valve. The alignment may be performed using imaging, such as fluoroscopy (e.g., three-dimensional fluoroscopy), which is used to locate the designated site and the direction of the tool(s) and to align the tool(s) such that when a treatment device (e.g., catheter) is inserted through the tool(s), the treatment device it will readily reach the designated site.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising a surgical closure device for anchoring to a tissue, which comprises:
    a continuous loop, which defines an opening therethrough, and which is configured to assume at least an open shape and a closed shape, wherein an area of the opening when the loop assumes the closed shape is less than 80% of the area of the opening when the loop assumes the open shape; and
    four or more tissue anchors, which are coupled to the loop, wherein each of said tissue anchors comprises a barb for irreversibly anchoring to the tissue,
    wherein the loop is configured such that, as the loop transitions from the open shape to the closed shape:
        all of the tissue anchors move in generally radial directions, and do not move in generally circumferential directions, and
        a first set of two or more of the tissue anchors move on average a first distance, and a second set of two or more of the tissue anchors move on average a second distance that is between 40% and 80% of the first distance.

2. The apparatus of claim 1, wherein, when the loop assumes the closed shape, said tissue anchors have a perpendicular orientation to the loop and extend in a same direction from the loop.

3. The apparatus of claim 1, wherein, when the loop assumes the closed shape, said tissue anchors have an orientation from 85 degrees to 95 degrees to the loop and extend from the loop into a space on a first side of a plane defined by the opening.

4. The apparatus of claim 1, wherein the tissue anchors extend from the loop into a space on a first side of a plane defined by the opening, when the loop assumes the closed shape.

5. The apparatus of claim 1, wherein the loop is flat in the open and the closed shapes.

6. The apparatus of claim 1,
    wherein the loop, when in the closed shape, is shaped so as to define two or more inwardly-extending portions, which extend toward a central region of the loop, and two or more outwardly-extending portions, which extend away from the central region, wherein the inwardly-extending portions alternate with the outwardly-extending portions around the loop, and
    wherein the tissue anchors are coupled to the loop such that when the loop assumes the closed shape, the first set of the tissue anchors are coupled to respective ones of the inwardly-extending portions, and the second set of the tissue anchors are coupled to respective ones of the outwardly-extending portions.

7. The apparatus of claim 6, wherein the tissue anchors are coupled to the loop such that when the loop assumes the closed shape, each of the tissue anchors of the second set is coupled to a most outwardly-extending location on its respective outwardly-extending portion.

8. The apparatus of claim 7, wherein the tissue anchors are coupled to the loop such that when the loop assumes the closed shape, each of the tissue anchors of the first set is coupled to a most inwardly-extending location on its respective inwardly-extending portion.

9. A method comprising:
    coupling a surgical closure device to a surface of cardiac tissue, using four or more tissue anchors of the closure device, which closure device includes a continuous loop that defines an opening therethrough, wherein each of said tissue anchors comprises a barb for irreversibly anchoring to the cardiac tissue, and wherein coupling comprises coupling while the loop assumes an open shape;
    forming a passage through the cardiac tissue that is surrounded by the loop; and
    after coupling, closing the passage by transitioning the loop to a closed shape such that, during the transitioning:
        all of the tissue anchors move in generally radial directions, and do not move in generally circumferential directions, and
        a first set of two or more of the tissue anchors move on average a first distance, and a second set of two or more of the tissue anchors move on average a second distance that is between 40% and 80% of the first distance.

10. The method of claim 9, wherein transitioning comprises transitioning the loop to the closed shape in which:
    the loop is shaped so as to define two or more inwardly-extending portions, which extend toward a central region of the loop, and two or more outwardly-extending portions, which extend away from the central region, wherein the inwardly-extending portions alternate with the outwardly-extending portions around the loop, and
    the first set of the tissue anchors are coupled to respective ones of the inwardly-extending portions, and the second set of the tissue anchors are coupled to respective ones of the outwardly-extending portions.

* * * * *